US009459192B2

(12) United States Patent
Hosoda et al.

(10) Patent No.: US 9,459,192 B2
(45) Date of Patent: Oct. 4, 2016

(54) WATER ABSORPTION TEST METHOD AND WATER ABSORPTION TEST DEVICE FOR CONCRETE SURFACE

(75) Inventors: Akira Hosoda, Kawasaki (JP); Kazuhiko Hayashi, Takamatsu (JP)

(73) Assignee: NATIONAL UNIVERSITY CORPORATION YOKOHAMA NATIONAL UNIVERSITY, Yokohama (JP)

( * ) Notice: Subject to any disclaimer, the term of this patent is extended or adjusted under 35 U.S.C. 154(b) by 331 days.

(21) Appl. No.: 14/008,819

(22) PCT Filed: Mar. 30, 2012

(86) PCT No.: PCT/JP2012/058605
§ 371 (c)(1),
(2), (4) Date: Sep. 30, 2013

(87) PCT Pub. No.: WO2012/133784
PCT Pub. Date: Oct. 4, 2012

(65) Prior Publication Data
US 2014/0013833 A1      Jan. 16, 2014

(30) Foreign Application Priority Data

Mar. 31, 2011  (JP) ................................. 2011-076916

(51) Int. Cl.
*G01N 9/36*      (2006.01)
*G01N 33/38*     (2006.01)
(Continued)

(52) U.S. Cl.
CPC .................. *G01N 9/36* (2013.01); *G01M 3/26* (2013.01); *G01N 15/08* (2013.01); *G01N 33/383* (2013.01)

(58) Field of Classification Search
CPC ...... G01N 9/36; G01N 33/383; G01M 3/042
See application file for complete search history.

(56) References Cited

U.S. PATENT DOCUMENTS

| 2009/0056437 A1* | 3/2009 | Kawanishi .............. G01F 23/14 73/295 |
| 2010/0070090 A1* | 3/2010 | Mirpourian ........... F24F 5/0085 700/278 |

FOREIGN PATENT DOCUMENTS

| CN | 201444105 U | 4/2010 |
| CN | 201575965 U | 9/2010 |

(Continued)

OTHER PUBLICATIONS

Machine Translation of Pertinent Sections of Hosoda et al., Effects of Microcrack of Surface Layer Concrete on Surface Absorption and Surface Permeability 2009, Cement Science and Concrete Technology, No. 63, pp. 196-198.*

(Continued)

*Primary Examiner* — Hezron E Williams
*Assistant Examiner* — David Z Huang
(74) *Attorney, Agent, or Firm* — Staas & Halsey LLP

(57) ABSTRACT

A water absorption property of a concrete surface of an actual structure is measured in situ for clarification and evaluation of causative factors and so forth related to densification of surface layer concrete. An apparatus for a water absorption test has a position-fixing device, a detecting device and a measuring device. A device for water absorption test having vent means is positionally fixed on the concrete surface by the position-fixing device, with use of negative pressure or a mechanical connection. The detecting device detects an amount of water held in a chamber, and results detected by the detecting device are input into the measuring device. A water absorption rate is measured by the detecting device and the measuring device. On the basis of the water absorption rate measured at predetermined elapsed time, identification or comparison of causative or evaluative factors related to densification of the surface layer concrete is carried out.

17 Claims, 19 Drawing Sheets

(51) Int. Cl.
*G01M 3/26* (2006.01)
*G01N 15/08* (2006.01)

(56) References Cited

FOREIGN PATENT DOCUMENTS

| JP | 2000-97748 | 4/2000 |
|---|---|---|
| JP | 2004-20511 | 1/2004 |
| JP | 2005-106724 | 4/2005 |
| JP | 2010-133708 | 6/2010 |
| WO | 98/29731 | 7/1998 |

OTHER PUBLICATIONS

Kyo et al., Study on Characterization of Hardened Concrete from Water Absorption-time Curve 2006, Key Engineering Materials vols. 302-303, pp. 500-507.*
International Search Report mailed Jun. 5, 2012 in corresponding International Application No. PCT/JP2012/058605.
British Standard 1881-5: 1970, "Method of Testing Concrete""Initial Surface Absorption Test", 5 pp.
A.E. Noble et al., "An automated method for the measurement of surface water absorption into permeable materials", Construction and Building Materials, vol. 9, No. 1, pp. 3-11, 1995.
Japanese Standards Association, "JIS A6909:2003, Coating materials for textured finishes of buildings", Edition 1, Japanese Industrial Standard, pp. 20-23.
"Water permeability test method for simply evaluating waterproof performance of water repellent for concrete", Concrete Research and Technology, Annual Academic Article, vol. 28, No. 1, pp. 2009-2014, 2006.
Ryoichi Ashizawa et al., "Research of Durability of Permeation-Type Water Absorption Preventive Material", Repair and Reinforcement of Concrete Structure, Upgrade Report of Academic Article vol. 10, Oct. 2010, pp. 393-398.
Akira Hosoda et al., "Effects of Microcrack of Surface Layer Concrete on Surface Absorbtion and Surface Permeability", Cement Science and Concrete Technology, No. 63/2009, Feb. 25, 2010, pp. 199-204.
Eitou Kyo et al., "Study on Characterization of Harden Concrete from Water Absorbtion-Time Curve", J. Struct. Constr. Eng., AIJ No. 556, pp. 1-6, Apr. 2003.
European Written Opinion mailed Nov. 11, 2014 in European Application No. 12765746.8.

* cited by examiner

Elapsed Time (sec.) from End of Water Pouring (A)

(B)

WATER ABSORPTION TEST METHOD AND WATER ABSORPTION TEST DEVICE FOR CONCRETE SURFACE

CROSS-REFERENCE TO RELATED APPLICATIONS

This application is a U.S. national stage application of PCT/JP2012/058605 filed Mar. 30, 2012 and claims foreign priority benefit of Japanese Application No. 2011-076916 filed Mar. 31, 2011 in the Japanese Intellectual Property Office, the contents of both of which are incorporated herein by reference.

TECHNICAL FIELD

The present invention relates to a method and apparatus for water absorption test of a concrete surface, and more specifically, to such a method and apparatus of a non-destructive type for in-situ measurement of a water absorption property of a surface of a concrete structure.

BACKGROUND ART

As an in-situ test method for evaluating durability of a newly-built or existing concrete structure, a non-destructive inspection or investigation directly measuring the mass transfer resistance is known in the art. In a constructed concrete structure, the resistance is reduced, owing to cracks, placing joints, construction joints and so forth, and therefore, the non-destructive inspection or investigation for investigating reduction of the resistance in the in-situ test is effective in evaluating the durability of the concrete structure.

An air permeability test focusing on transfer of air, or a water permeability test or a water absorption test focusing on transfer of water are known as a method for directly measuring the mass transfer resistance. It is considered that deterioration of concrete relates to chemical reaction, physical action and so forth in which water is participated. For instance, a case is exemplified in which corrosion of steel materials in reinforced concrete does not occur in a condition of extremely dry environment, even if carbonation of concrete progresses to the extent that the carbonation reaches the steel materials. Therefore, it is important to grasp the transfer of water for clarifying the deterioration of concrete.

A water pressure acting on an actual and usual structure is a relatively low pressure, which acts on its surface owing to rainfall and so forth. Pore diameters and a mass transfer mechanism dominating the mass transfer differs, depending on variation in fluid pressure acting on the concrete. Therefore, the test is preferably carried out under a condition equivalent to the ambient environment surrounding the actual structure, that is, under a condition that a relatively low pressure, such as a water head of approximately 200-300 mmAq, acts on the concrete surface. In the water permeability test, however, the water pressure of several newtons per mm$^2$ is usually imposed on the concrete surface. This may increase the water permeability after the water permeability test, owing to destruction of a concrete texture. Therefore, in general, it is considered that the water absorption test is effective, wherein the concrete surface is merely subjected to a water pressure corresponding to a pressure naturally acting on the concrete surface during rainfall.

"British Standard 1881-5" "Method of Testing Concrete" "Initial Surface Absorption Test" (non-patent literature No. 1), which is referred to as "ISAT" hereinafter, is known as a surface water absorption test for measuring an amount of water absorbed through a concrete surface by concrete. In this test method and its test device, the amount of absorbed water is measured in a condition that the water pressure of 200 mmAq acts on the concrete surface. The water pressure of 200 mmAq is a pressure slightly higher than the water pressure acting on the concrete surface during heavy rainfall. Further, in "An automated method for the measurement of surface water absorption into permeable materials" (non-patent literature No. 2), the measuring method is disclosed, in which water absorption properties of water permeable materials are measured with use of a capillary tube and a sophisticated optical measuring device. Furthermore, a water permeability test method with respect to coating materials for building finishing works is disclosed in "JIS A6909-2003 coating materials for building finishing works" (non-patent literature No. 3). The test of JIS A6909-2003 is a water absorption test or water permeability test for paint and so forth, wherein the test is conducted with use of a specimen coated with the paint and so on to be applied to the concrete surface or the like.

However, the test methods and the test devices as set forth above are merely methods and devices for conducting measurement of water absorption properties or water permeabilities of horizontal surfaces of concrete specimens in laboratories. In other words, they are not the test methods and the test devices for in-situ measurements of water absorption properties or water permeabilities of vertical surfaces and so forth with respect to actual structures, which are land fixtures affected by external factors (ambient environmental conditions, construction conditions and so forth). That is, the test devices and methods disclosed in the non-patent literatures Nos. 1 to 3 are not intended for in-situ non-destructive tests for investigating the surface water absorption properties of the actual structures. Further, it may be considered that samples extracted from the actual structures are tested for investigating their water absorption properties in accordance with the test methods as disclosed in the non-patent literatures Nos. 1 to 3. However, as regards the water absorption test method for the actual structures newly-built, it is difficult to employ the test methods involved in extraction of the specimens therefrom. Further, even in a case where the specimens are extracted from the existing structures built in the past, the positions or locations of the structures, from which the specimens can be extracted, are limited. In addition, it is necessary to repair or mend the structures after the tests.

Further, a test method accompanying drilling of a hole in an actual structure is known in the art as a conventional water absorption test method. However, such a test is an in-situ test resulting in damage of the actual structure. Therefore, this is not the non-destructive test of the actual structure.

On the other hand, water absorption test devices are disclosed in non-patent literatures Nos. 4 and 5, wherein water absorption tests are conducted with respect to existing concrete structures with its surface coated with silane system water-repellent agent. Each of the test devices disclosed in the non-patent literatures Nos. 4 and 5 is so arranged that a circular cup with a vertical pipette in a form of tube is secured on a wall surface of an actual structure and that an in-situ measurement of an amount of water absorbed by a concrete surface thereof is carried out by measuring reduction of water filled in the cup.

Furthermore, an in-situ test device with a simple arrangement is known in the art, which comprises a water absorption cup of a small size fixed to a vertical concrete surface without destruction thereof, wherein a base plate of the cup is fixed to the vertical concrete surface by vacuum pressure.

CITATION LIST

Non-Patent Literature

[Non-Patent Literature No. 1]
"British Standard 1881-5" "Method of Testing Concrete" "Initial Surface Absorption Test"
[Non-Patent Literature No. 2]
"An automated method for the measurement of surface water absorption into permeable materials" (Construction and Building Materials, Vol. 9, No. 1, pp. 3-10, 1995)
[Non-Patent Literature No. 3]
"JIS A6909-2003, Coating materials for building finishing works"
[Non-Patent Literature No. 4]
"Water permeability test method for simply evaluating waterproof performance of water repellent for concrete" (Concrete Research and Technology, Annual Academic Article Vol. 28, No. 1, pp. 2009-2014, 2006)
[Non-Patent Literature No. 5]
"Research of Durability of Permeation-Type Water Absorption Preventive Material" (Repair and Reinforcement of Concrete Structure, Upgrade Report of Academic Article Vol. 10, October 2010)

SUMMARY OF INVENTION

Technical Problem

In general, the quality of surface layer concrete can be evaluated by its densification. Further, a concrete structure exhibits its expected strength by means of corporative action of concrete and steel bars. Since the bars in the concrete is protected by the surface layer concrete, the durability of concrete of the actual structure remarkably differs, depending on the densification of the surface layer concrete. However, the conventional water absorption test is merely directed to investigation of water-proofing effect or water-resistant effect of water repellant agent, paint, priming coat and so forth, or detection of cracks of the concrete surface. That is, the results of water absorption tests are not used for evaluation of the densification of the surface layer concrete.

The densification of the surface layer concrete differs, depending on design conditions, construction conditions, a water-cement ratio of concrete during construction, a mix proportion of concrete (use of expansive additive or the like), a curing period and curing method of concrete, and so forth. Further, the densification of the surface layer concrete also differs, depending on environmental conditions (climates, solar radiation, gravity and the like), a hydration exothermic reaction of cement, a restrained condition of the concrete structure, use of a surface-impregnated material (water repellant and the like), and so forth. Thus, if evaluation and clarification of the densification of the surface layer concrete can be made by an in-situ water absorption test, it would be possible to retroactively suppose or specify the condition of concrete during construction work or historical information of concrete during its curing process or after curing, by means of the in-situ water absorption test. However, approach to analysis of the results of the water absorption test has not been tried in relation to a causative factor of densification of the surface layer concrete and so forth.

Further, in a case of the conventional in-situ water absorption test as disclosed in the non-patent literatures Nos. 3 and 4, the amount of water absorbed by the concrete surface is merely measured by visually observing a variation of the water level in a cylinder part of the absorbed water chamber. The variation of the water absorption cannot be continuously measured nor measured at short time intervals successively.

Furthermore, it is preferable that the water absorption test is a completely non-destructive test which is applicable to a final inspection of a newly-constructed structure. However, in the test device as disclosed in the non-patent literatures Nos. 4 and 5, the water absorption cup has to be adhered to a vertical concrete surface by a putty-like silicone, fast cure type epoxy resin or the like, and therefore, a fixation mark or trace of the test device leaves on the concrete surface. Accordingly, it is necessary to grind the concrete surface after the test in order to eliminate the mark or trace. Therefore, the tests as disclosed in the non-patent literatures Nos. 4 and 5 are not the completely non-destructive test.

On the other hand, the aforementioned water absorption test device is known, in which the base plate is secured on the vertical surface by vacuum pressure. As regards this device, the diameter of the water absorption cup is merely about 25 mm and the water absorption opening area thereof is merely about 490 mm$^2$. Even if such a cup having a small diameter and a small opening area is used, its circumferential length is large relative to the water absorption area. Therefore, influence of a quantity of water diffusing to the periphery of the cup is significant, and it is difficult to correctly measure the amount of water absorbed by the concrete surface.

Thus, a water absorption test device and method of the completely non-destructive type, which is applicable to the actual structure without destructing the concrete, have not been developed yet.

Further, if water for a test is rapidly poured into a water absorption cup in a conventional water absorption test device, air bubbles remain in the cup. Therefore, at least one minute is ensured for pouring the water, and therefore, the initial water absorption of the concrete surface, which occurs before one minute elapses from the beginning of pouring water, cannot be measured. However, the concrete surface has a property in that capillary water absorption rapidly occurs immediately after contact with the water. That is, the conventional test device cannot measure the initial water absorption of the concrete surface which occurs before one minute elapses from the beginning of pouring water. Therefore, the test cannot sufficiently clarify the water absorption property of concrete.

The object of the present invention is to provide a water absorption test method which can carry out in-situ measurement of water absorption property of a surface layer concrete for clarification and evaluation of causative factors and so forth which relate to the densification of the surface layer concrete.

Further, the object of the present invention is to provide a water absorption test apparatus preferably used in such a water absorption test method for performing a completely non-destructive type of water absorption test, in which the concrete surface and the surface layer concrete are not destructed at all.

Furthermore, the object of the present invention is to provide such water absorption test apparatus and method for initiating the measurement of the water absorption test at an early stage (preferably, within 15 seconds after the beginning of water pouring).

Solution to Problem

For achieving the above objects, the present invention provides a method for a water absorption test of a concrete surface, in which an edge portion of an opening part of a water absorption cup is brought into intimate contact with the concrete surface of a concrete structure, water for the test is poured into a water absorption chamber in the cup, and an amount of water absorbed from the chamber by the concrete structure is measured in situ;

wherein the amount of water held in said chamber is continuously detected or successively detected at small time intervals, in order to measure a water absorption rate and elapsed time from an end of water pouring, and wherein identification or comparison of causative or evaluative factors related to densification of surface layer portion of concrete is carried out on the basis of the water absorption rate measured at a predetermined elapsed time.

According to the above arrangement of the present invention, the amount of water absorbed by the concrete surface is substantially continuously detected after the end of water pouring, and variation of the amount of absorbed water in relation with elapsed time from the end of water pouring, that is, the water absorption rate is detected. It is possible to carry out identification or comparison of the causative factors (or causative indications) or evaluative factors (or evaluation indications) related to the densification of the surface layer concrete. For instance, the recent research of the present inventors clarified that there is a specific relationship among the water absorption rate at the elapsed time of 10 minutes, a water-cement ratio during construction work, a curing period of concrete (the term before removal of a concrete form) during the construction work. Each of the water-cement ratio and the curing period is a kind of causative or evaluative factor closely related to the densification of the surface layer concrete. That is, information of the causative or evaluative factors related to the densification of the surface layer concrete can be obtained by measurement of the water absorption ratio, whereby the quality of the surface layer concrete can be evaluated objectively.

Further, in accordance with the above test method, it is possible to carry out statistical processing or data processing of the relations between the elapsed time from the end of water pouring and the water absorption ratio, with respect to a number of actual structures. According to the recent research of the present inventors, the actually measured values of the water absorption rate at a predetermined elapsed time tend to conform to the normal distribution or Gaussian distribution. Therefore, the actually measured values of the water absorption rate are adequate to the statistical processing or data processing. This means that the water absorption test can be used as a quality inspection method of the surface layer concrete which is necessary to preset a threshold.

Furthermore, in some of the actual structures, the records of construction works still remain, which reveal the causative factors or evaluative factors regarding the densification (water-cement ratios, periods of curing, and so forth). In such cases, a database regarding the relationship between the water absorption rates and the causative or evaluative factors can be established by statistical processing of the rates and the factors. This means that it is possible to carry out identification or comparison of the factors related to the densification of the surface layer concrete on the basis of the database, if the test method of the present invention can be appropriately applied to the actual structure which is not provided with clear records of the construction work or which is necessary to confirm the construction condition, design condition and so forth retroactively after the construction work even if the records of the construction work still remain.

The present invention also provides an apparatus for a water absorption test of a concrete surface of a concrete structure, which has a water absorption cup provided with a water absorption chamber to be filled with water for an in-situ water absorption test, wherein said cup has an opening part surrounded by an edge which can be in intimate contact with the concrete surface, and the water in said chamber is in contact with said concrete surface through the opening part and is absorbed by the concrete surface, comprising:

a detecting device provided with a detecting element for continuously detecting an amount of water held in said chamber, or successively detecting said amount of water at small time intervals, and a measuring device which indicates or records an amount of absorbed water and elapsed time from an end of water pouring, wherein a result detected by said detecting device is input into the measuring device.

According to the above apparatus of the present invention, the amount of the water absorbed by the concrete surface can be detected substantially continuously, and the absorption rate can be measured in relation with the elapsed time after the end of water pouring. Therefore, the aforementioned test method can be easily carried out by the present apparatus.

Preferably, the detecting device is a water pressure sensor which detects a water pressure in the chamber, and the amount of the absorbed water is detected by the water pressure in the chamber. A detecting element of the water pressure sensor is inserted into the chamber in order to detect the water pressure at or near a lowermost part of the chamber. More preferably, the measurement device includes means for converting the detected value of the sensor to the amount of absorbed water, and means for calculating the water absorption ratio on the basis of change or variation in the amount of absorbed water per unit time. The variation of the water level of the cylinder part can be accurately detected (for example, by the accuracy less than 1 mm) by detecting the variation of the water pressure in the chamber. In the conventional water absorption test depending on visual observation, one observer can simultaneously observe merely two or three water absorption devices even if the devices are located at relatively near positions. However, the water absorption test of the present invention, in which the water pressure in the chamber is detected, enables simultaneous tests at a number of points or remote points with use of the many apparatuses.

Preferably, the "small time interval" is time equal to or less that 10 seconds, and the aforementioned opening part has an area equal to or larger than 5000 mm$^2$. This value of the area corresponds to the lower limit (5000 mm$^2$) defined in the aforementioned ISAT. More preferably, the cup has vent means for urging exhaust of air bubbles in the chamber when pouring the water into the chamber. According to experiments of the present inventors, the air bubbles can be prevented from remaining in the cup during the water pouring, by provision of the vent means in the cup, whereby the speed of pouring the water is accelerated to considerably reduce the term of time for the water pouring. The vent means is a downward spreading portion provided at a lowermost part of a passage of the cylinder part (a water-head tube), or inclination given to an inner wall surface of the cup on which the passage opens. The apparatus provided with such vent means allows the water pouring operation to be completed within 15 seconds, preferably 10 seconds (averagely 5 seconds), and therefore, measurement of the amount of water absorbed by the concrete surface can be initiated within 15 seconds (preferably, within 10 seconds) after the beginning of the water pouring. According to such early start of measurement, the amount of absorbed water can be measured at an initial stage before one minute elapsing from the beginning of water pouring, and therefore, it is possible to precisely grasp the water absorption property of the concrete surface.

Preferably, the present apparatus includes a position-fixing device for fixing the position of the cup. The fixing device comprises a transverse beam spaced apart from the concrete surface, a pressing device carried by the beam for pressing the cup against the concrete surface, and a holding device which holds the position of the beam and integrally connects the beam with the concrete structure. The holding device is provided with a sticking means which sticks to the surface of the concrete structure under a negative pressure, or mechanical connector means which is threadedly engaged with an existing threaded member embedded in the concrete structure. The sticking means or the connector means connects the beam to the concrete structure by a force which exceeds a reaction force of the pressing device acting on the beam. More preferably, the sticking means includes a sticking part which can stick on the concrete surface, a negative pressure chamber sealingly confined between the sticking part and the concrete surface, and connecting means for connecting the negative pressure chamber to a pressure-reducing device which sucks the air in the negative pressure chamber. Further, the existing threaded member is a separator at least partially embedded in the concrete structure, and the connector means is a connector provided with a threaded portion threadedly engaged with a thread of the separator.

According to such an apparatus, the cup is integrally connected with the concrete surface by means of the negative pressure acting on the concrete surface, or a mechanical connection with the existing member embedded in the concrete structure, and therefore, damage of the concrete structure is avoidable. Thus, according to the apparatus with such arrangement, a mark or trace of the cup, which needs a grinding treatment, does not leave on the concrete surface after removal of the cup, and therefore, the completely non-destructive type of in-site water absorption test can be carried out, in which the mark or trace never leaves on the actual structure. In addition, the apparatus with the above arrangement allows the cup to be easily and quickly installed on the concrete surface of the actual structure.

From another aspect, the present invention can be applied to a water permeability test method and apparatus for measuring a water permeability of the concrete surface. In such a case, pressurizing means in association with the cup is further provided for pressurizing the water in the cup up to a predetermined pressure.

Advantageous Effects of Invention

According to the water absorption test method of the present invention, the in-situ measurement of the water absorption property of the concrete surface can be carried out with respect to the actual structure, and causative factors and so forth related to the densification of the surface layer concrete can be clarified and evaluated.

According to the water absorption test apparatus of the present invention, an apparatus preferably used for such a water absorption test method can be provided.

Further, according to the apparatus of the present invention arranged to fix the position of the cup with use of the negative pressure or the mechanical connection, it is possible to perform the completely non-destructive type of water absorption test, which never destructs the concrete surface and the surface layer concrete.

Furthermore, according to the test and the apparatus with use of the aforementioned vent means for urging the exhaust of air bubbles, the water pouring operation can be completed in a short time and the measurement of the amount of absorbed water can be stated in an early stage (preferably, within 15 seconds after the beginning of water pouring).

BRIEF DESCRIPTION OF DRAWINGS

FIG. 3 includes cross-sectional views and a side elevational view generally showing the apparatus according to the present invention, wherein FIG. 3(A) is the cross-sectional view taken along line I-I of FIG. 2 and FIG. 3(C) is the cross-sectional view taken along line II-II of FIG. 2.

FIG. 4 includes a plan view and a cross-sectional view generally showing the apparatus according to the present invention, wherein FIG. 4(B) is the cross-sectional view taken along line III-III of FIG. 2.

FIG. 8 includes vertical cross-sectional views schematically showing a mode of water pouring operation, wherein FIG. 8(A) shows a state immediately before the water pouring operation and FIG. 8(B) shows a condition during the water pouring operation.

FIG. 9 includes vertical cross-sectional views schematically showing another mode of the water pouring operation, wherein FIG. 9(A) shows a condition immediately before the water pouring operation and FIG. 9(B) shows a condition during the water pouring operation.

FIG. 12 includes graphic charts showing results of the in-situ water absorption test automatically measured with respect to the actual structures by the apparatus according to the present invention, wherein FIG. 12(A) shows the time variation of the accumulated amount of absorbed water, and FIG. 12(B) shows the time variation of the water absorption rate calculated on the basis of the accumulated amount of absorbed water.

EMBODIMENT

With reference to the attached drawings, a preferred embodiment of the present invention is described hereinafter.

Figure 1:
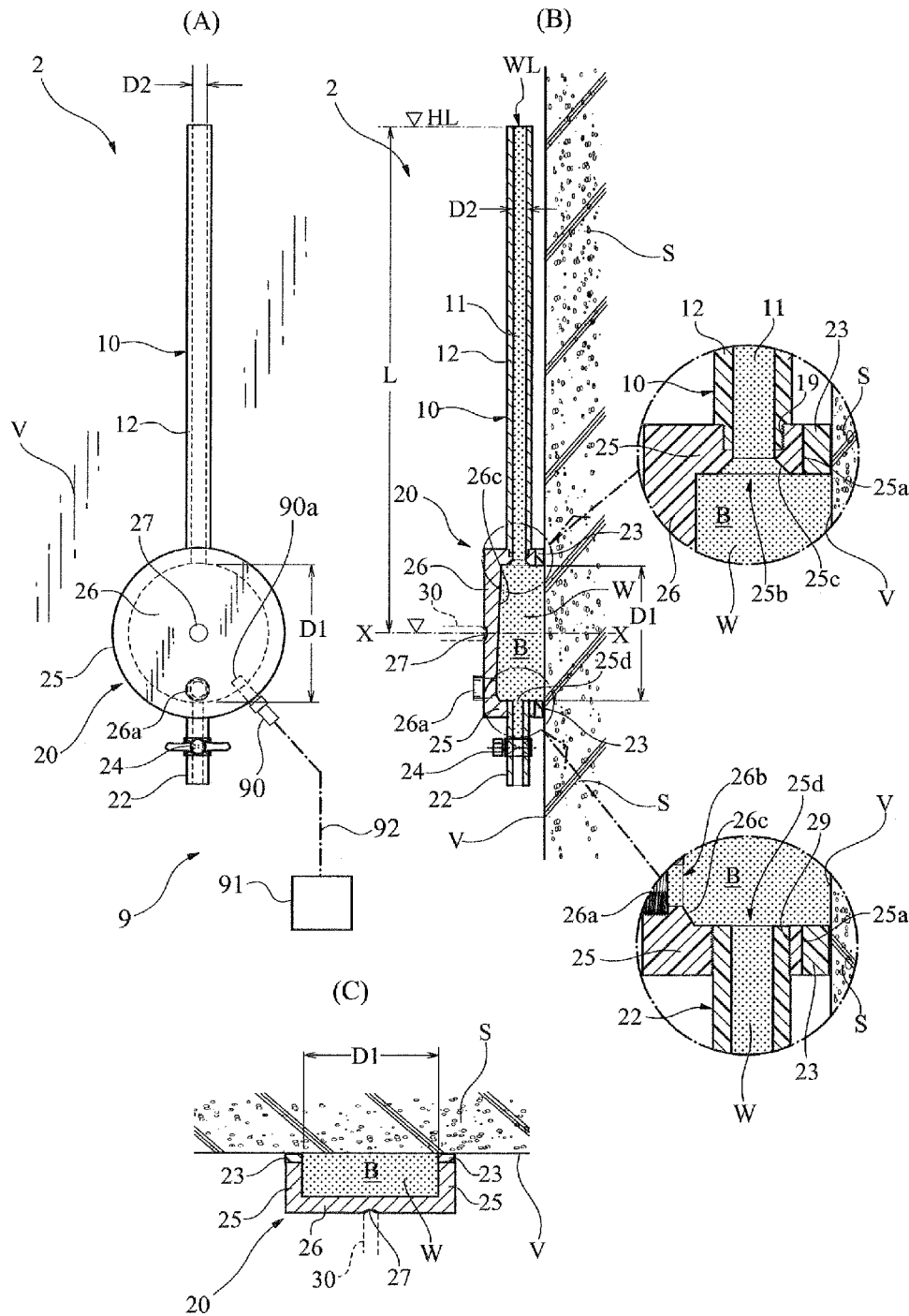
FIG. 1 includes a front elevational view, a vertical cross-sectional view, partially enlarged cross-sectional views and a horizontal cross-sectional view which show a device for water absorption test constituting an apparatus for water absorption test, wherein the device is installed on a vertical wall surface.
Figure 2:
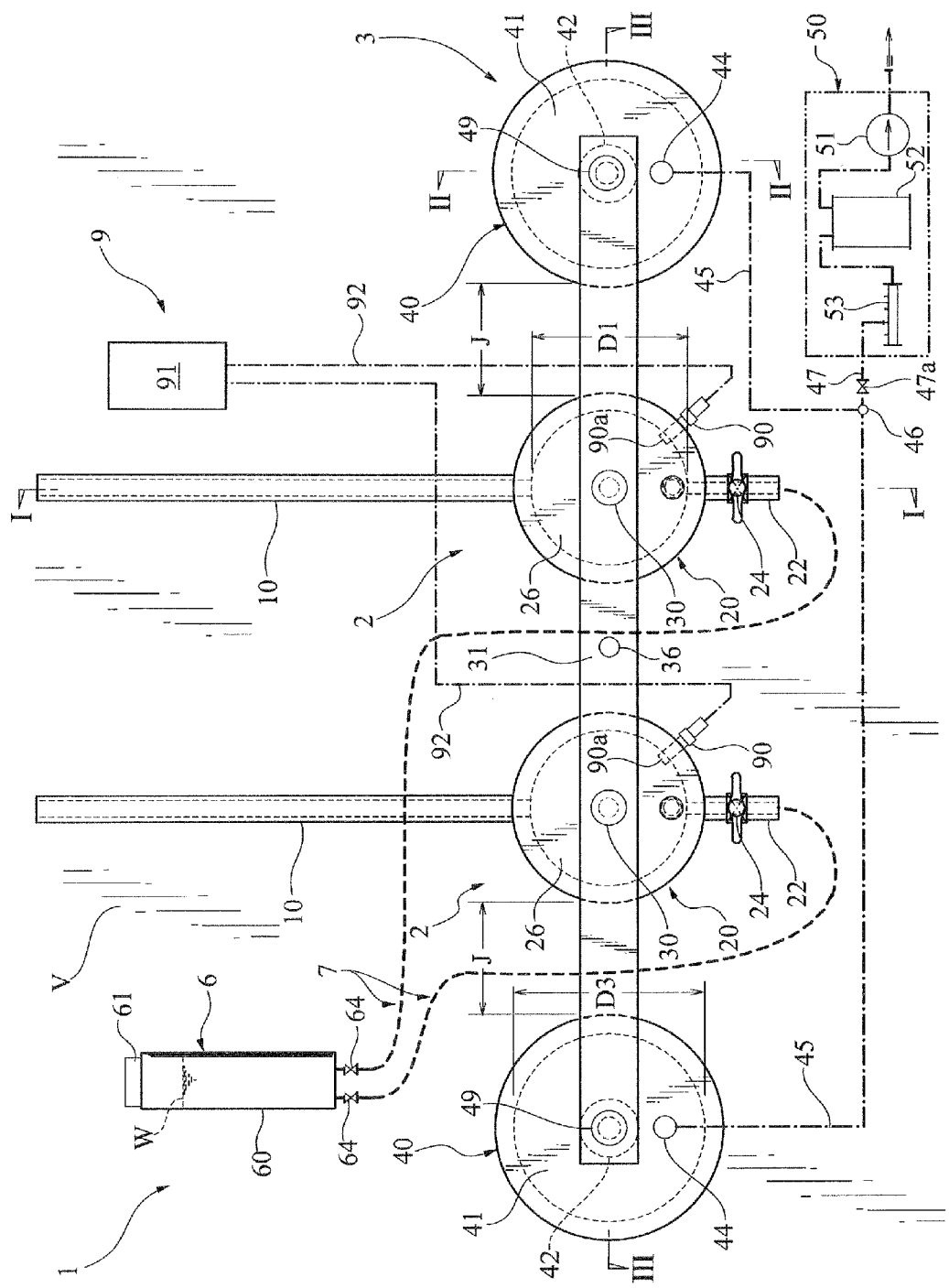
FIG. 2 is a front elevational view generally showing the apparatus according to the present invention.
Figure 3:
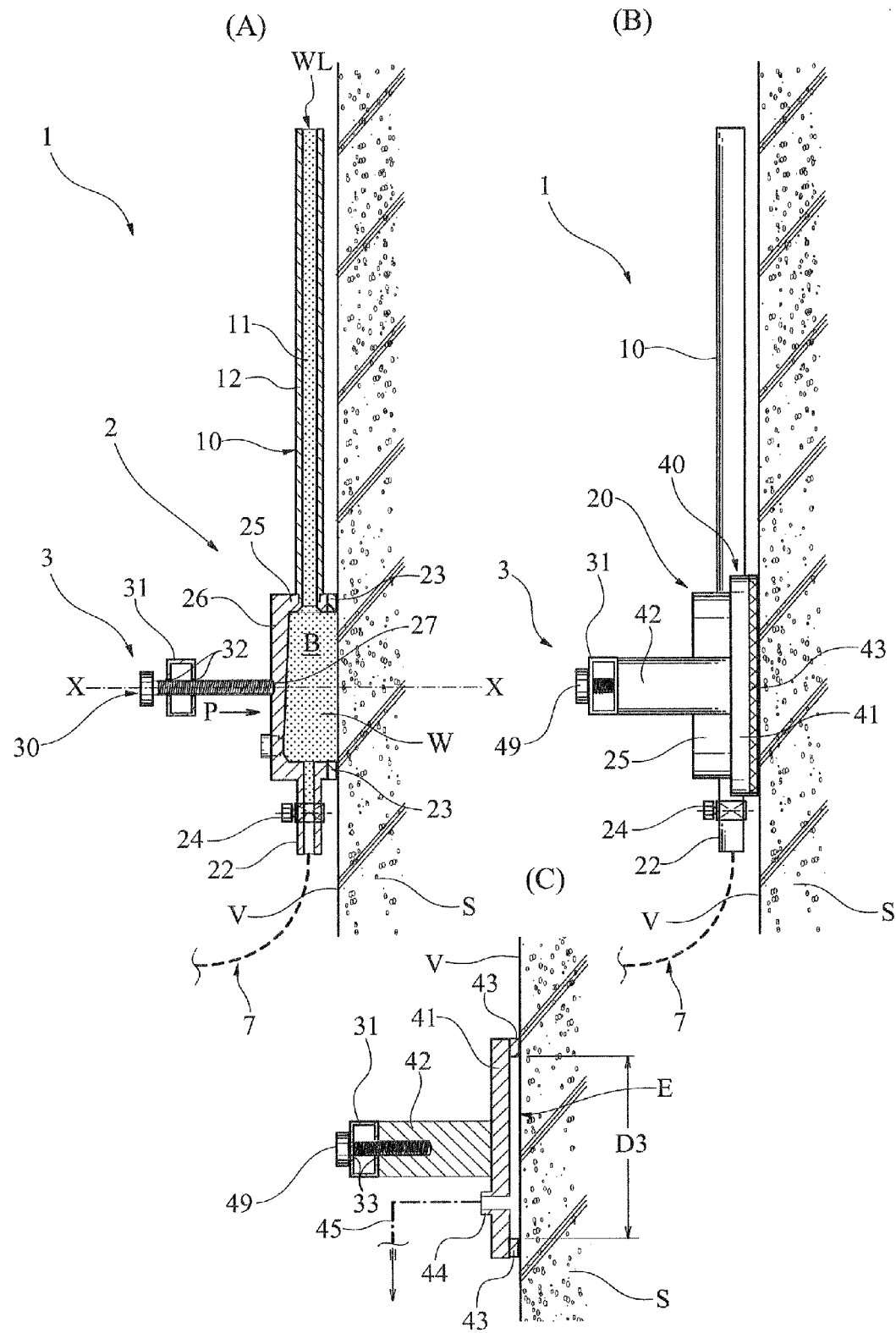
Figure 4:
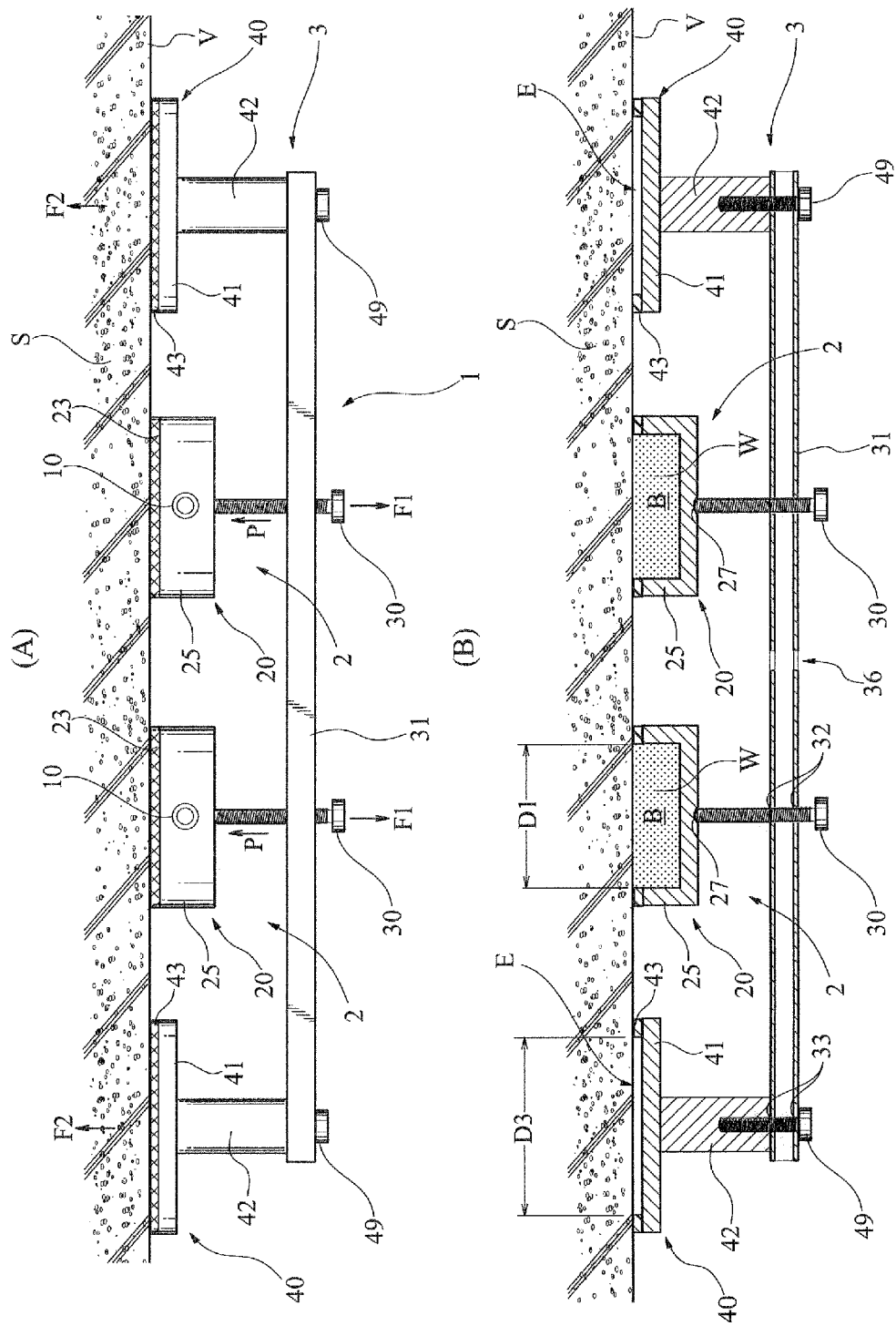

A device for water absorption test 2 is shown in FIG. 1, which constitutes an apparatus for water absorption test 1. The arrangement of the apparatus 1 is generally shown in FIGS. 2 to 4. The apparatus 1 comprises the device 2, a position-fixing device 3, a water supply appliance 6 and a water level measuring means 9. The device 2 enables the water to be absorbed from a vertical surface V of a concrete structure S. The device 3 allows the device 2 to be fixed on the surface V in position. The appliance 6 is used for pouring the water into the device 2. The measuring means 9 automatically measures and records a water level of a water surface WL.

As shown in FIG. 1, the device 2 is constituted from a water absorption cup 20, a graduated tubular cylinder part 10, a drain tube 22 and an elastically deformable annular sealing member 23. The cup 20 is positionally fixed to the surface V, the cylinder part 10 extends from an uppermost or topmost part of the cup 20 vertically upward, the tube 22 extends from a lowermost or bottommost part of the cup 20 vertically downward, and the sealing member 23 is integrally attached to an edge portion of an opening part of the cup 20 adjacent to the surface V. Each of the cup 20, the cylinder part 10 and the tube 22 is constituted from transparent materials or parts integrally assembled by water-tight joining means, such as welding or an adhesive material. Each of the cup 20, the cylinder part 10 and the tube 22 may be integrally molded from the transparent resin. The cup 20, the cylinder part 10 and the tube 22 are integrally assembled by the water-tight joining means, such as screw joints, welding, an adhesive material or the like. In this embodiment, an external thread 19 provided at a lower end portion of the cylinder part 10 is screwed into an internal thread provided at the uppermost part of the cup 20, and an external thread provided at an upper end portion of the tube 22 is screwed into an internal thread provided at the lowermost part of the cup 20. In use, the cup 20 is pressed against the surface V by a fixing screw 30 of the device 3 as shown by dotted lines, so that the sealing member 23 is brought into water-tight contact with the surface V under a cramping pressure of the screw 30.

In FIG. 1, the cup 20 is a condition of being filled with water. As shown in FIG. 1, the cup 20 comprises a cylindrical peripheral wall 25 having a round cross-section, and a circular disc 26 closing a circular outside opening of the wall 25. An absorbed water chamber B is formed by the wall 25 and the disc 26. A dent 27 for receiving a tip of the screw 30 as shown by the dotted lines in FIG. 1(B) is formed at a center of the disc 26. The sealing member 23 is cramped between an opening edge 25a of the peripheral wall and the surface V, so as to prevent leakage of the water in the cup 20. In this embodiment, the inner diameter D1 of the wall 25 is 80 mm, and the area of the surface V in contact with the water W in the chamber B is 5024 $mm^2$. This value is substantially equal to the minimum value (5000 $m^2$) defined in the aforementioned ISAT.

The conduit passage 11 in the cylinder part 10 leads to chamber B by means of a circular opening 25b at the uppermost part of the wall 25, so as to be in communication with an area (the chamber B) inside of the cup 20. The opening 25b has a spreading portion 25c in a tapered form. The cylinder part 10 is a tube having an inner diameter D2=8 mm. The passage 11 extends vertically upward from the opening 25b. The spreading portion 25c constitutes vent means for urging exhaust of air bubbles in the chamber B, so that the air bubbles in the chamber B rapidly moves into the passage 11 when pouring the water thereinto. The water of the cup 20 is filled with the passage 11 up to an initial level HL, and the water in the cup 20 is continuous with the water in the passage 11. A tube wall 12 is provided with a scale (not shown) graduated thereon for visual observation. The scale is used as indication of the position of the water level WL. The position of the water level WL can be visually measured from its outside. If desired, the tube having an enlarged or reduced inner diameter D2 (e.g., the tube with D2=6 mm) may be used as the cylinder part 10 for adjustment or change of sensitivity of measurement.

A vertical distance L between the initial water level HL and a horizontal center line X of the cup 20 is set to be 300 mm, and therefore, the average water head acting on the surface V is initially set to be 300 mm. According to this value of the water head, the water pressure, which is slightly larger than the water head acting on the surface V when raining, substantially uniformly acts thereon. The water level WL gradually drops, owing to a water absorption effect of the concrete on the surface V.

A circular opening 25d in communication with a passage of the drain tube 22 is formed at the lowermost part of the wall 25. The tube 22 has an inner diameter equal to or equivalent to the inner diameter of the tube 11, such as 8 mm in diameter. The tube 22 has a valve 24 for manual operation. The valve 24 normally closes the passage of the tube 22.

The sealing member 23 is made of a rubber sponge of a closed cell type (Specified Hardness Value: 25±5 degree indicated by Asker Durometer Type C). The rubber sponge has a square or rectangular cross-section, the width of which is substantially the same as the width of an annular zone of the edge 25a, e.g., 10 mm in width. The thickness of the sealing member 23 (initial thickness) is set to be 5 mm. As shown in FIG. 3(A), the tip portion of the screw 30 abuts against an inner surface of the dent 27. The cup 20 is pressed against the surface V by tightening the screw 30, whereby the sealing member 23 is elastically and compressively deformed under pressure. Although the concrete of the surface V has minute irregularity or unevenness, the sealing member 23 fits on the concrete surface by its elastic deformation. The rubber sponge of the sealing member 23 is a closed cell type of porous material and therefore, it has little water absorbing property. However, the sealing member 23 is preferably used after it is preliminarily impregnated with water, since a cut surface or an exposed surface of the rubber sponge is porous. Further, depending on the situation of the existing concrete structure, cement paste or mortar of its surface may be partially lost owing to its aged deterioration, so that coarse aggregate, fine aggregate and so forth may be exposed on the surface V. Even in such a case, the sealing material 23 is in intimate contact with the surface V by its deformation, and therefore, the water in the chamber B can be prevented from leaking outside of the cup 20.

The apparatus for water absorption test 1 including the position-fixing device 3 is generally shown in FIGS. 2 to 4. As set forth above, the devise 3 presses the cup 20 against the surface V by means of the screw 30. A butterfly screw, a screw with knurling or a bolt with a bolt head for manual tightening may be used as the screw 30. The device 3 includes a transverse beam 31 extending over the plurality of cups 20 (the two cups 20 in this embodiment), and right and left suckers 40 in a pair integrally attached to end portions of the beam 31. The beam 31 is made of a hollow metal tube having a square or rectangular cross-section. The beam 31 is provided with screw holes 32 (FIG. 3(A)). Each of the screws 30 extends through each of the holes 32 and is threadedly engaged with the hole 32. As illustrated in FIGS. 2 to 4, the sucker 40 comprises a circular disc 41 having a diameter of approximately 120 mm, a column part 42 having a circular cross-section and fixed to a center part of the disc 41, and an annular sealing member 43 having an inner diameter D3=100 mm. In FIG. 4(A), there is illustrated a pressing force P and a reaction force F1 acting on the beam 31 in response to the pressing force P.

Each of the disc 41 and the column 42 is integrally molded from a transparent or semi-transparent resin. An outside end of the column 42 is secured to an end portion of the beam 31 by a retainer 49, such as a bolt for manual operation. As the retainer 49, a butterfly screw, a screw with knurling or a bolt with a bolt head for manual tightening may be used. The sealing member 43 is made of a rubber sponge of a closed cell type which is the same as that of the sealing member 23. The sealing member 43 has a rectangular or square cross-section, which is the same as that of the sealing member 23, e.g., the rectangular cross-section of 10 mm in width and 5 mm in thickness. The sealing member 43 is in intimate contact with the surface V airtightly, and a suction chamber E is defined by the disc 41 and the sealing member 43.

As shown in FIG. 2, the right and left suckers 40 are provided with suction ports 44 respectively, which constitute connecting means for connecting with a pressure-reducing device. The ports 44 are connected with flexible tubes 45 made of elastically deformable resin tubes, respectively. The tubes 45 extending from the ports 44 of the suckers 40 are connected with a flexible tube 47 by means of a coupling 46.

The tube 47 is provided with a manually operable valve 47a and is connected with a pressure-reducing device 50. The device 50 includes a vacuum pump 51, a buffer tank 52 and a header 53. The pump 51 is a small-size dry pump, the displacement of which is 17 liters per minute and the operation capacity of which is approximately 100V, 1A. Such a pump can be supplied with electric power by a compact generator, an inverter for a vehicle, or the like. Alternatively, a DC power supply type of vacuum pump with the same displacement and capacity may be used as the pump 51, whereby the pump 51 may be operated by a DC battery.

The pump 51 is connected with the header 53 in series through the buffer tank 52 acting as buffer means. The tube 47 is selectively connected with one of connection ports of the header 53. The pump 51 sucks air in the chamber E when opening the valve 47a to reduce the pressure of the chamber E. The sucker 40 is energized toward the surface V by the reduced pressure so that the sealing member 43 is brought into intimate contact with the surface V under the suction pressure. Thus, the right and left suckers 40 are secured on the surface V under the negative pressure of the chamber E, and the beam 31 is suspended between the right and left columns 42. A suction force F2 of each of the suckers 40 obtained by the reduction in pressure of the chamber E is shown in FIG. 4(A). The force F2 is larger than the reaction force F1 acting on the beam 31 so as to cancel the reaction force F1.

In FIG. 2, the tank 52 is a pressure tank having a capacity of approximately one liter. The tank 52 prevents the position of the water level WL from seemingly varying owing to influence of change in pressure of the pump 51 acting on the chamber E, which may be otherwise caused during measurement. The header 53 constitutes branching means for connecting the device 50 with the plurality of apparatuses 1, whereby the plurality of apparatuses 1 can be used simultaneously. In this embodiment, the pump 51 is used only for securing the sucker 40 to the surface V. The negative pressure of the chamber E may be substantially constant during the water absorption test. According to the experiments of the present inventors with use of actual structures, stable support of the beam 31 can be attained by approximately $-0.08$ N/mm$^2$ for the wall surfaces (the surfaces V) of newly constructed structures and approximately $-0.06$ N/mm$^2$ for the wall surfaces (the surfaces V) of existing structures. Preferably, the cup 20 and the sucker 40 are spaced apart from each other, at least a distance J (FIG. 2) of 50 mm (in this embodiment, J is approximately 60 mm), in order to prevent the negative pressure of the sucker 40 from affecting the cup 20. Further, it is possible to support the three or more cups 20 by the device 3. However, in the visual inspection of the water level, one observer is to perform tests with use of the cups 20 at intervals of 30 seconds. Therefore, it would be difficult for the observer to simultaneously perform visual inspection with use of the four or more cups 20.

The water level measuring means 9 of the apparatus 1 comprises a water pressure sensor 90 and an automatic recording system 91. The sensor 90 is connected with the system 91 by means of a control signal line 92. A detecting element 90a of the sensor 90 extends through the wall 25 in vicinity of the lowermost part of the chamber B, so that the element 90a is in contact with the water in the cup 20. As the sensor 90, a highly accurate water pressure sensor may be preferably used, which can outputs a voltage of 4 volts per a pressure change of 20 kPa corresponding to change of the water head of 2 m (2000 mm). Such a sensor can detect change of the water head of 1 mm as 0.0005V (0.5 mV). As the system 91, a data logger can be preferably used, in which accuracy of detection is 0.05 mV (the resolution is 0.1 mm in change of the water level). According to such an apparatus 1, the water absorption tests can be carried out with use of the many devices 2, or the tests can be carried out simultaneously with use of the plurality of apparatuses 1, and further, change in the water level WL of each of the devices 2 can be measured and recorded continuously or at intervals of very short unit time.

The experiments conducted by the present inventors have clarified that the measurement in millimeters can be performed with use of the sensor 90, with few errors of measurement. A handy-type of data logger with a battery may be used for simplification of in-situ measurement. Further, it is possible to graphically show the change in the water level, the change in the water absorption rate, and so forth. It is also possible to additionally use a programmable controller, PC or the like for automatically recording and displaying the water absorption rate and so forth.

Figure 5:
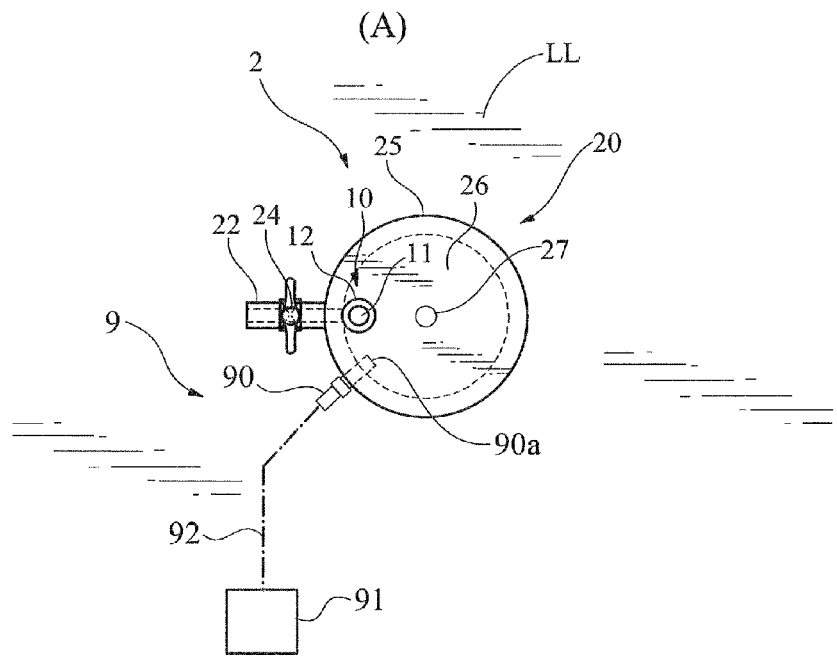
FIG. 5 includes a plan view, a vertical cross-sectional view and a partially enlarged cross-sectional view illustrating a condition of the apparatus installed on a horizontal concrete surface.
Figure 5:
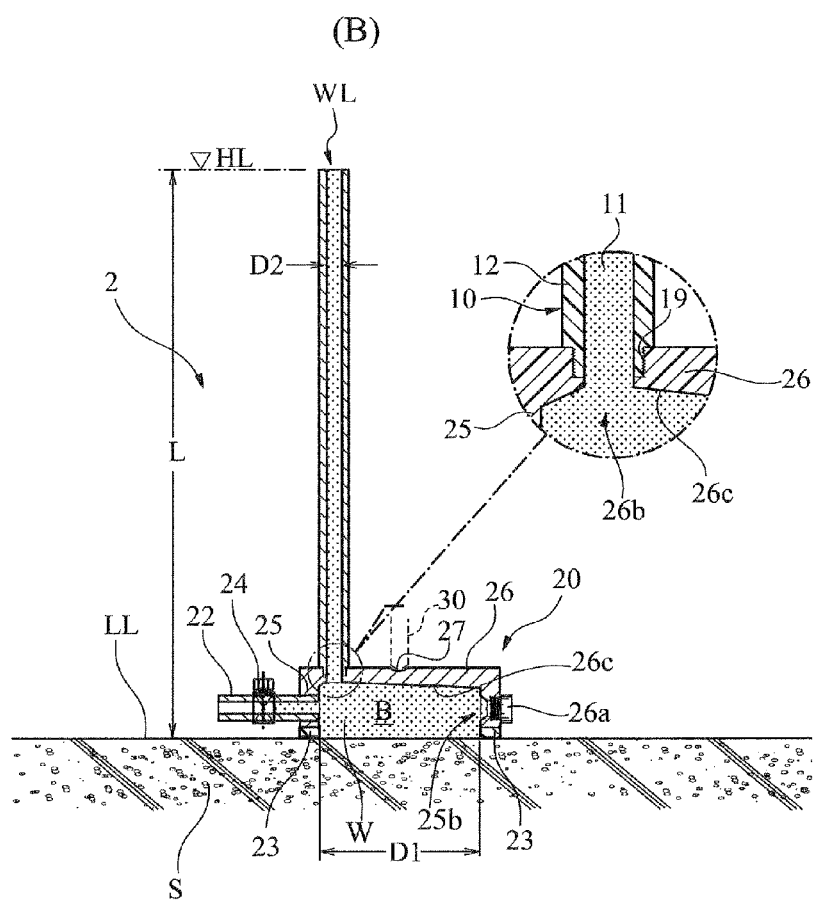

If desired, the apparatus 1 of this embodiment may be installed on a horizontal surface or an inclined surface. FIG. 5 shows a state in that the device 2 is installed on a horizontal surface LL of the concrete structure S. The cup 20 is placed on the surface LL with the opening of the chamber B being directed downward. The beam 31 (FIG. 2) is secured to the surface LL under the negative pressure of the sucker 40, and is suspended between the right and left columns 42 (FIG. 2). The cup 20 is pressed against the surface LL by the screw 30 of the device 3 (shown by dotted lines in FIG. 5(B)), so that the sealing member 23 is brought into intimate contact with the surface LL in a water-tight condition under the tightening pressure of the screw 30.

The disc 26 of the cup 20 has a circular opening 26b, into which the lower end portion of the cylinder part 10 can fit. The external thread 19 provided at the lower end part of the cylinder part 10 is screwed into the internal thread provided at the opening 26b. An inner surface (underside surface) of the disc 26 is inclined upward toward the opening 26b, so that air or air bubbles in the cup B rapidly move into the passage 11. The inclination of the inner surface (underside surface) of the disc 26 constitutes the vent means.

In a case where the device 2 is located on the horizontal surface LL as set forth above, a plug 26a is screwed into the opening 25b of the wall 25 to close the opening 25b. On the other hand, when the device 2 is located on the vertical surface V, the plug 26a is screwed into the opening 26b so that the opening 26b is normally closed, as shown in FIG. 1.

A testing method in use of the apparatus 1 with respect to the vertical surface V is described hereinafter.

At first, the device 3 is positioned on the vertical surface V of an actual structure (a concrete structure S) as shown in FIG. 2. The actual structure is, e.g., a bridge abutment of a reinforced concrete structure, and the surface V is a wall surface thereof. Then, the pump 51 of the device 50 is operated to reduce the pressure of the chamber E of the sucker 40, so that the sucker 40 is securely fixed on the surface V by the suction force F2 (FIG. 4). The device 2 is positioned on the surface V in such a manner that the tip of the screw 3 aligns or matches with the dent 27. In this condition, the chamber B has not been fed with the water yet.

As shown in FIG. 4, the screw 30 is tightened against the beam 31, so that the tip of the screw 30 generally presses the cup 20 against the surface V. The sealing member 23 is elastically deformed by the pressure P of the screw 30, so that the member 23 is brought into intimate contact with the concrete surface. Thus, installation of the apparatus 1 is rapidly completed in a very simple operation.

Figure 6:
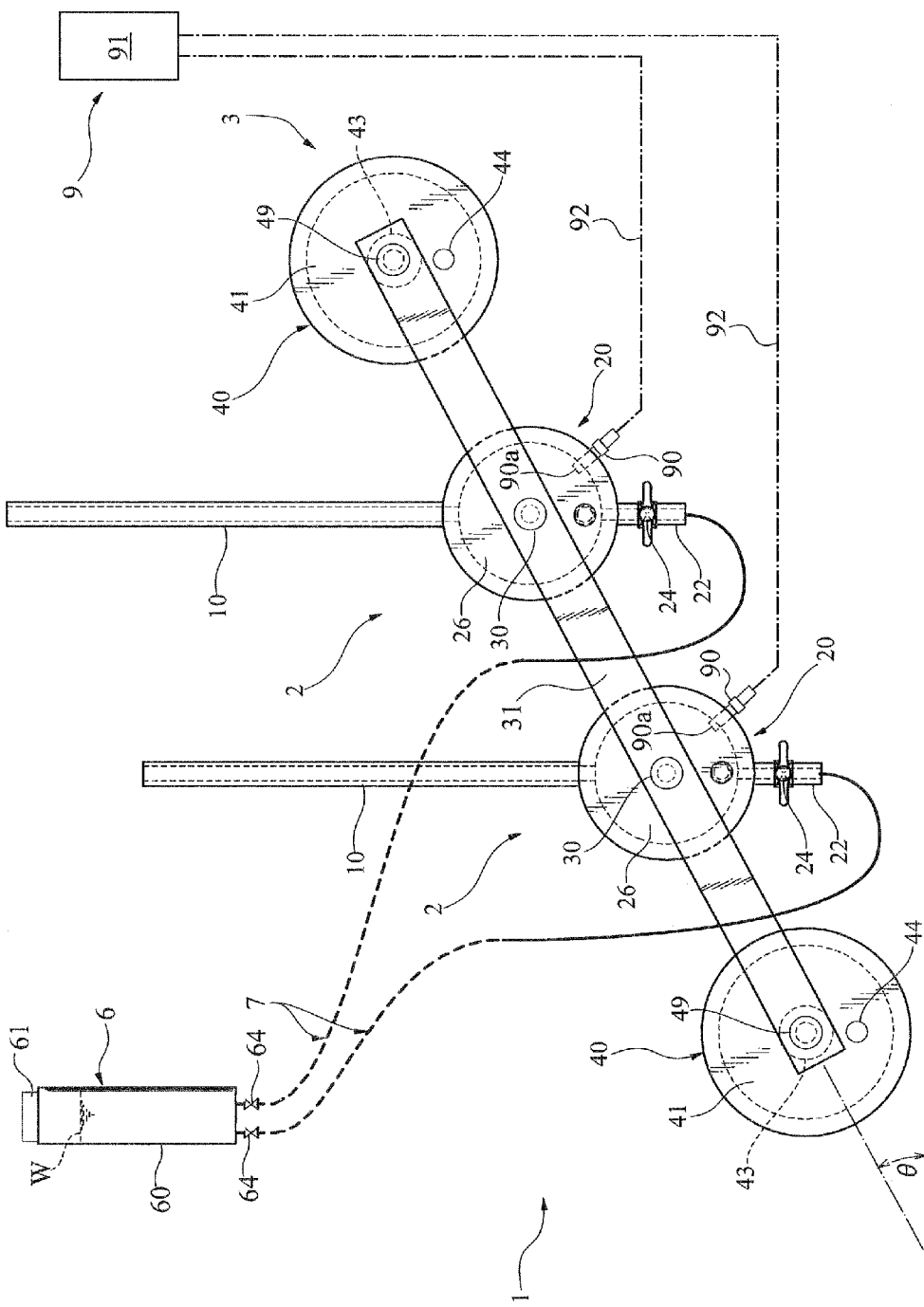
FIG. 6 is a front elevational view showing a condition of installation in which the two devices are located in a vertically offsetting relative position.

The relative position of the devices 2 is not necessarily limited to be a horizontally aligned formation. As shown in FIG. 6, the devices 2 may be arranged in a vertically offsetting relative position. In such case, the beam 31 is inclined at an angle of θ with respect to the horizontal plane.

Then, the water for water absorption test is poured into the device 2. As the water for the test, city water is used for preventing the concrete surface from clogging or the like. If the temperature of the water significantly differs from the outdoor temperature or the temperature of the concrete surface, it is preferable that the temperature of the water is preliminarily adjusted to be the outdoor temperature for preventing the water from changing its volume, owing to change in the water temperature during the test.

Figure 7:
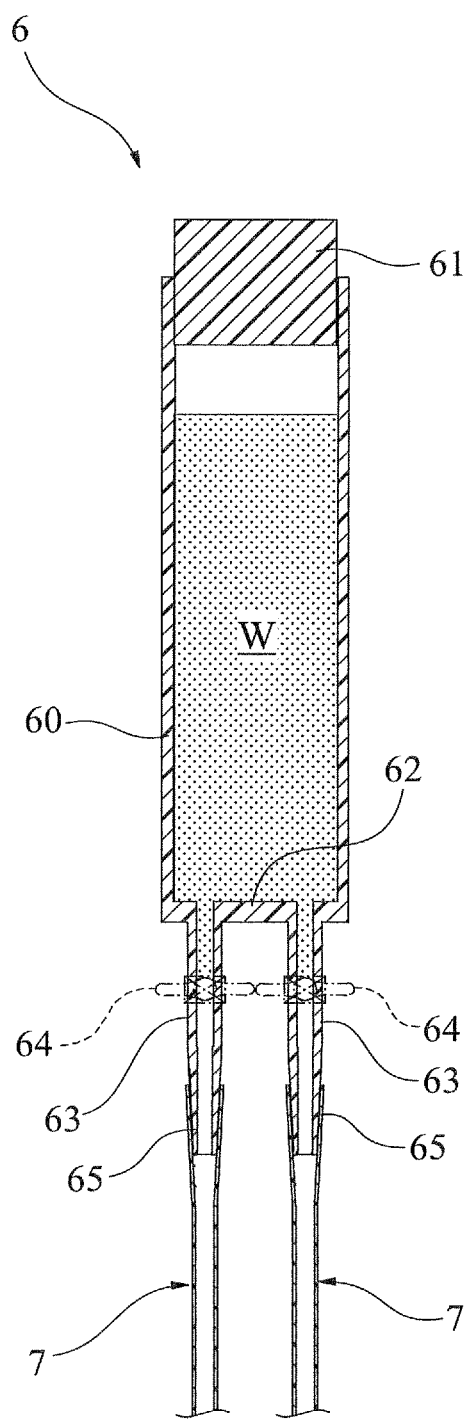
FIG. 7 is a vertical cross-sectional view schematically showing a structure of a water pouring appliance for pouring water into the device.

An arrangement of a water pouring appliance 6 is shown in FIG. 7, which is used for pouring the water into the device 2. The appliance 6 comprises an open top type of cylindrical container 60, a cap 61 for closing a top circular opening of the container, a pair of water pouring ports 63 extending downward from a bottom part 62 of the container 60. The ports 63 have manually operable valves 64, respectively. Flexible tubes for water pouring 7 is connected with diameter-reducing sections 65 at lower end portions of the ports 63, and the tubes 7 lead to the chambers B of the cups 20. The container 60 and the ports 63 are made from transparent or semi-transparent resin, and the cap 61 is a rubber or resin plug which can fit into the opening of the container 60. Each of the valves 64 is a metal or resin valve. The tube 7 is an elastically deformable tube made from transparent resin. Each of the sections 65 of the ports 63 is fit into an upper end opening of the tube 7.

Figure 8:
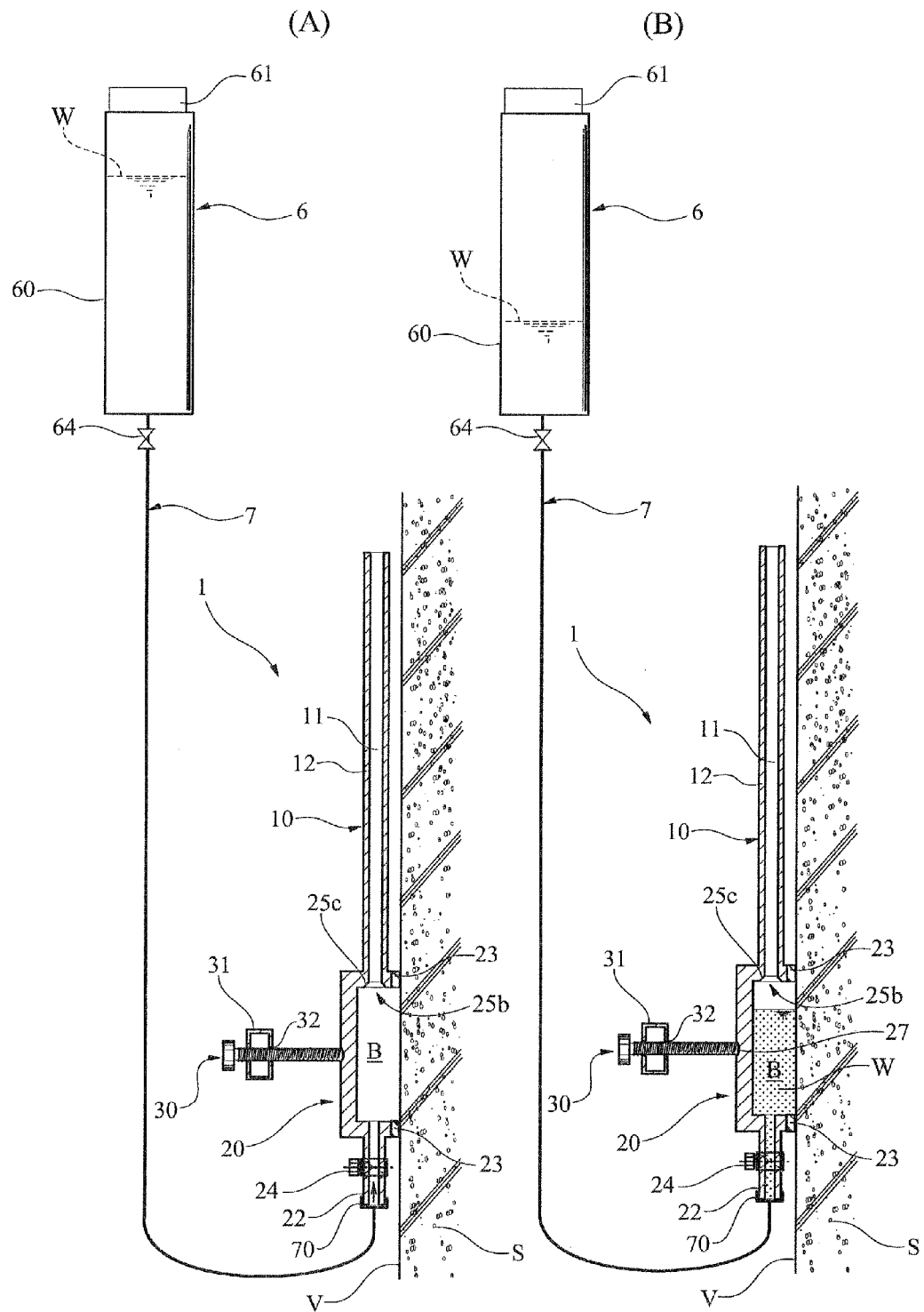

A typical operation for water pouring is generally illustrated in FIG. 8. In the water pouring operation, a predetermined quantity of water W (city water) is accommodated in the container 60, and a fitting or connector 70 at a leading end of the tube 7 is connected with a lower end portion of the drain tube 22 (FIG. 8(A)). The water W in the container 60 is poured into the cup 20 gravitationally (FIG. 8(B)). The water W in the container 60 gradually increases the volume from its bottom. The air or air bubbles in the cup 20 smoothly flows into the passage 11, owing to existence of the vent means (the spreading portion in a tapered form 25c), and is discharged to the atmosphere through the top opening of the passage 11. Therefore, the water level WL of the water W rises rapidly. When the water level WL of the water W rises up to the uppermost part of the passage 11 (the initial water level HL as shown in FIG. 1), the valves 24, 64 are closed. The tube 7 is extracted from the tube 24 appropriately.

Figure 9:
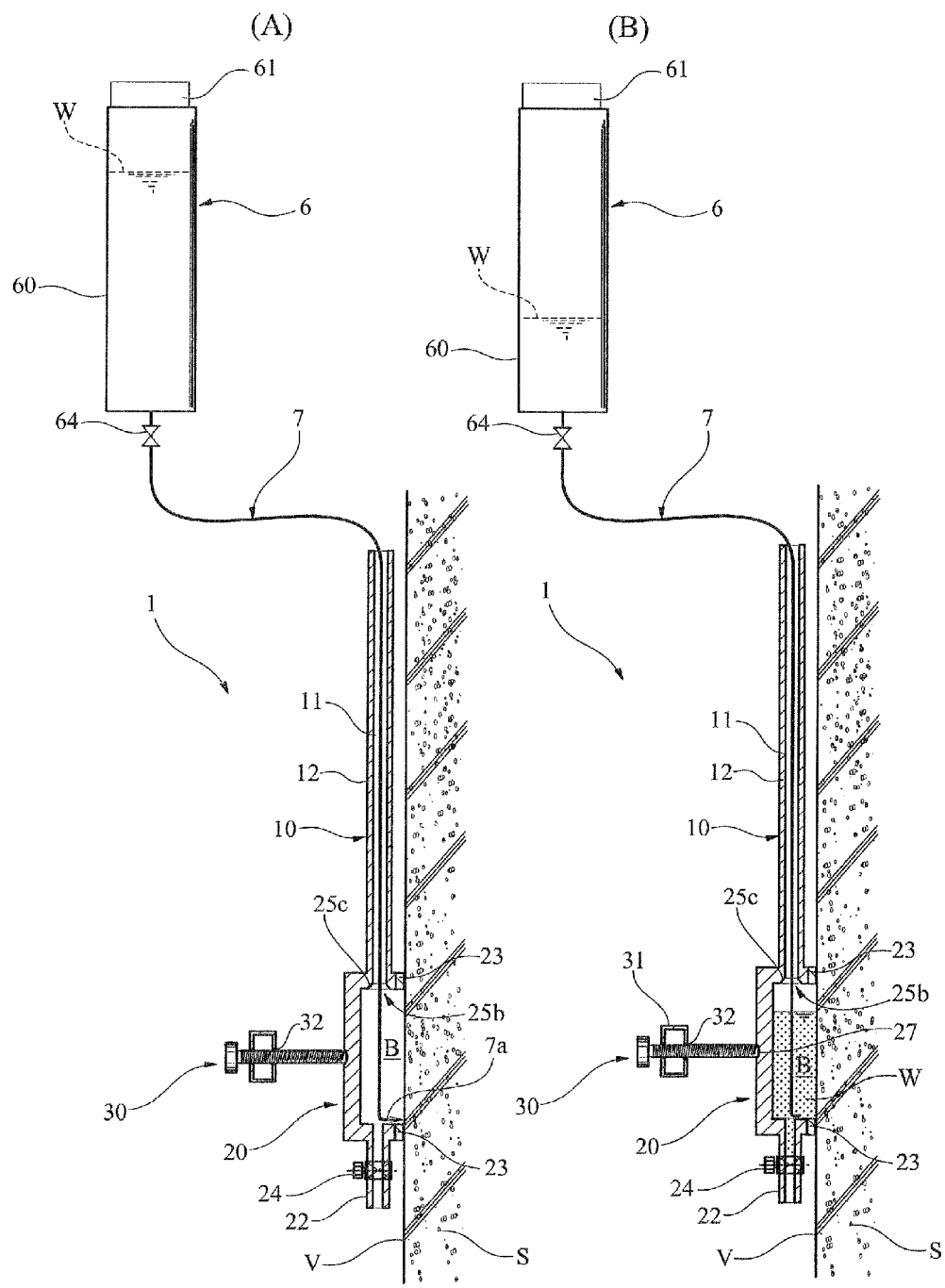

In FIG. 9, another mode of operation for water pouring is generally illustrated. In the operation as shown in FIG. 9, a predetermined quantity of water W (city water) is accommodated in the container 60, and then, the tube 7 is inserted into the tube 11 of the cylinder part 10, so that a leading end opening 7a of the tube 7 is positioned at the lowermost part of the chamber B (FIG. 9(A)). Thereafter, the valve 64 is opened and the water W gradually increases the volume from the bottom of the cup 20. The air or air bubbles in the cup B smoothly flows into the passage 11, owing to existence of the vent means (the spreading portion 25c), and is discharged to the atmosphere through the top opening of the passage 11. Therefore, the water level WL of the water W rises rapidly. The tube 7 is lifted in relation to rising of the water level while the location of the opening 7a is kept under the water surface. When the water level WL rises up to the uppermost part of the tube 11 (the initial level HL as shown in FIG. 1(B)), the valve 64 is closed and the tube 7 is fully extracted from the passage 11, and thus, the water pouring operation is completed.

In such an operation, since the cup 20 with the vent means (the spreading portion 25c) has an arrangement in that the air or air bubbles are hard to remain in the water of the chamber B, and the air or air bubbles in the cup 20 are swiftly exhausted through passage 11. Therefore, the water pouring operation can be performed very simply and rapidly. According to the experiments of the present inventors, the pouring operation in such a mode can be completed in a term of time equal to or less that 10 seconds (approximately 5 seconds averagely). The measurement is carried out immediately after completion of the water pouring operation. The measurement is performed by continuously measuring and recording the change of the water surface WL with use of the water level measuring means 9, wherein a starting point of the measurement is the water head (L=300 mm) obtained when finishing the water pouring operation. If desired, visual observation of the position of the water level WL is carried out with use of the scale on the cylinder part 10 and a stopwatch for measuring time, in addition to the automatic measurement as set forth above. After the water absorption test is completed, the water remaining in the cup 20 is discharged through the drain tube 22 by manually opening the valve 24.

The present inventors attached the apparatus 1 to an actual structure, and poured water into the device 20, and then, carried out the automatic measurement with use of the measuring means 9 and the visual observation as set forth above, wherein the initial water level was the water head=300 mm at the time of finishing the water pouring operation. In the visual observation, the position of the water surface WL was read in millimeters with use of the scale on the cylinder part 10, in time intervals of one minute. In a case where the testing time is approximately 60 seconds, it is possible to neglect vaporization of water from the top opening of the tube 11. However, in a case where the measurement is performed for a long time more than 60 seconds, it is preferable that the top opening of the tube 11 is covered with any covering means for preventing the vaporization. If necessary, it is desirable that the temperature of the concrete surface is measured by a non-contact type thermometer and that the water content of the surface layer concrete is measured by a moisture meter of two-points surface contact type, an electric resistivity test means on the basis of a tetra-polar method, or the like.

The instantaneous rate of water absorption is obtained by a differential calculus equation as shown by the following formula (1), in which the rate is defined by the amount of water absorbed through the concrete surface per unit time and unit area.

$$y = dx/dt \quad (1)$$

wherein, "y" represents the instantaneous rate of water absorption (ml/m$^2$/sec), "x" represents the accumulated amount of the absorbed water (ml) per the unit area of the concrete surface (m$^2$), and "t" represents time (second).

In a case of the visual observation, the position of the water level WL is read from the graduation of the cylinder 10, change in the water level WL is converted to the accumulated amount of the absorbed water "x", and the instantaneous rate of water absorption "y" is obtained on the basis of the time interval in the measurement. On the other hand, in a case of continuous measurement using the automatic recording system 91, the value of the instantaneous rate of water absorption "y" is directly or indirectly obtained from the visual indications or the outputs of the system 91.

The present inventors conducted experiments with respect to an abutment of bridge and a box culvert with use of the apparatus 1. The outline of each of those structures is as follows:

(1) Abutment of Bridge
  Age: 8 years
  Cement: Portland blast-furnace cement, class B
  Condition of the Structure: A number of micro-cracks are observed near construction joints and separators. The condition of the concrete surface is dry.

(2) Box Culvert
  Age: 7 years
  Cement: Portland blast-furnace cement, class B
  Condition of the Structure: The inside of the structure is a space where sunlight is blocked and the humidity therein is normally high, and therefore, the condition of the concrete surface is wet.

Figure 10:
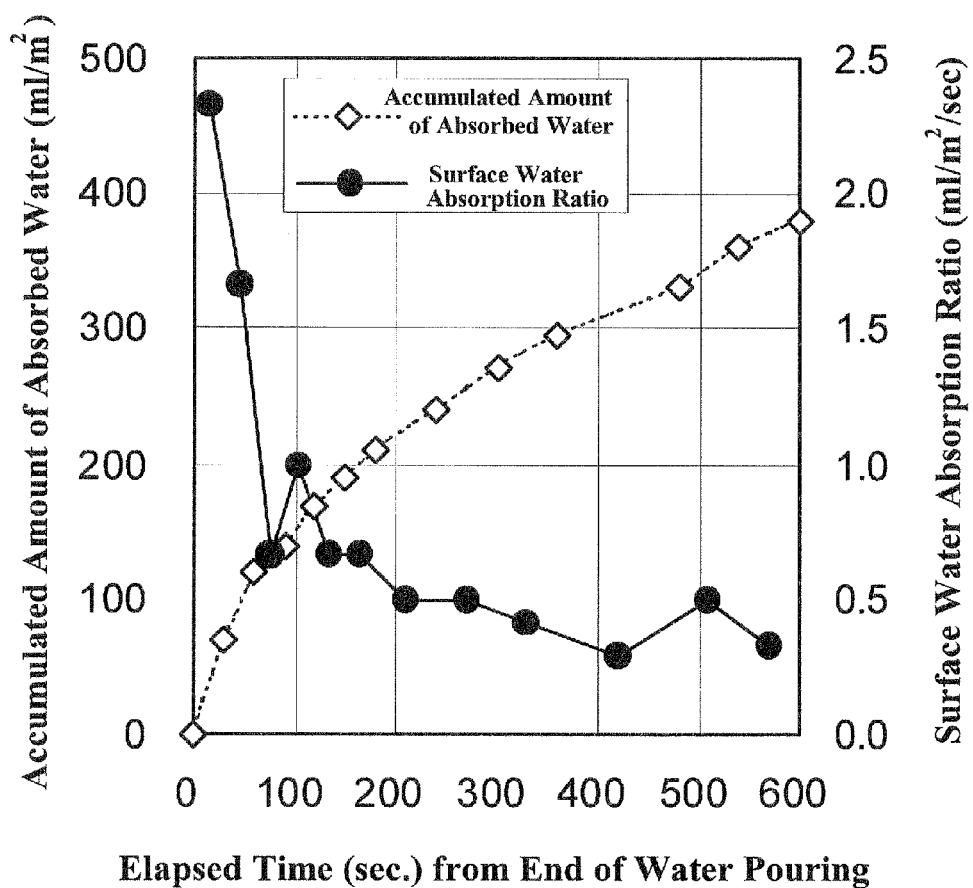
FIG. 10 is a graphic chart showing results of a water absorption test with respect to an actual structure, which are measured by visual observation, wherein an accumulated amount of absorbed water measured from the end of the water pouring operation (at 15 seconds elapsed from the beginning of the water pouring operation) and time variation of a surface water absorption ratio (water absorption rate) are indicated.

FIG. 10 is a graphic chart showing the variation of the accumulated amount of absorbed water measured in the water absorption test with respect to the actual structure (abutment of bridge) by visual observation. The measurement was started when the water pouring operation was finished (when 15 seconds elapsed from the beginning of water pouring). In FIG. 10, the vertical axis on the left side indicates the accumulated amount of absorbed water, and the vertical axis on the right side indicates the water absorption rate (surface water absorption ratio) in relation to time. The water absorption rate is an average value obtained by dividing the amount of absorbed water per unit area by the interval time between measurements. As is understandable from FIG. 10, the water absorption rate indicates its maximum value immediately after finishing the water pouring, and the rate gradually decreases thereafter. Especially, the rate in an initial period of an approximately 2 minutes is remarkably large in comparison with the rate in the succeeding period and thereafter.

In a research report of M. Levitt (Non-destructive Testing of Concrete by the initial surface absorption method, Proceedings of a Symposium on Non-Destructive Testing of Concrete and Timber, London, June 1969, Institution of Civil Engineers, pp. 23-26, 1970), he proposed the following formula (2) for logically representing the water absorption rate;

$$y = a \times t^{-n} \quad (2)$$

wherein "a" and "n" are constants.

The constant "a" in the above formula (2) is a parameter representing the water absorption rate at the time of one second elapsing from the beginning of the water pouring. The constant "a" mainly relates to the densification (the quality) of the concrete surface. The constant "n" is, in general, set to be a value in a range of 0.5±0.2. The constant "n" is a parameter representing temporal variation of the amount of absorbed water, which indicates a degree of reduction in the water absorption ratio. The constant "n" mainly relates to the densification of the internal concrete (surface layer portion). The larger constant "n" means the better densification (the higher quality) of the internal concrete. However, the above theoretical equation merely indicates the water absorption property of a theoretical and idealized homogeneous porous texture.

Figure 11:
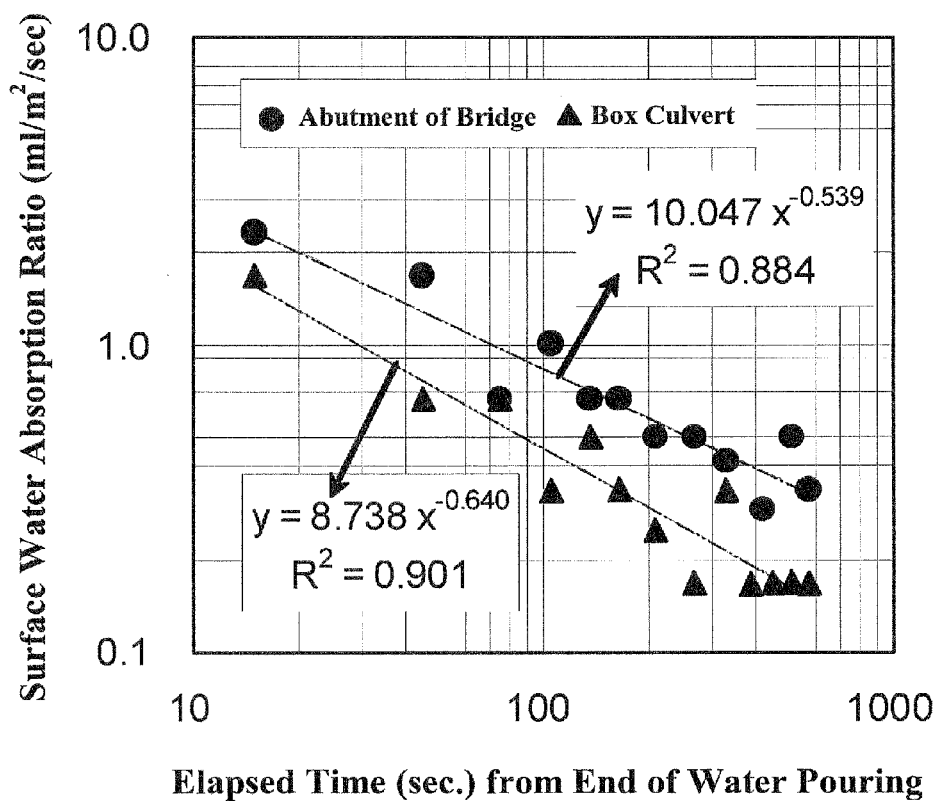
FIG. 11 is a graphic chart showing a relation between the surface water absorption ratios (water absorption rates) measured by the visual observation of the actual structures (an abutment of a bridge and a box culvert) and line segments of the surface water absorption ratios obtained by Levitt's theoretical equation.

It has been already confirmed that the above equation approximately conforms to the results of water absorption tests with respect to concrete specimens, which were measured when 10 minutes, 30 minutes and 60 minutes elapsed after the beginning of water pouring, respectively. Further, in the aforementioned non-patent literature No. 2, the results of water absorption tests with respect to concrete specimens prepared for the test are disclosed, wherein the measurement results are those obtained at time intervals in minutes. Furthermore, in the aforementioned non-patent literature No. 2, compatibility between the results of the tests and the Levitt's theoretical equation is described. FIG. 11 is a graphic chart showing the relation between the water absorption rates (surface water absorption ratio) measured by visual observation and the water absorption rates obtained by the above formula (2), with respect to the actual structures of the abutments and the box culverts as set forth above, wherein the relation in FIG. 11 is indicated by log-log graphic scale. In a case where the water pouring operation is finished within approximately 15 seconds, the relation between the measured value of the water absorption rate and the elapsed time generally approximates or conforms to the values obtained by the above theoretical equation (the formula (2)). The values of the constant "n" obtained by the measurement are n=0.539 for the abutment and n=0.640 for the box culvert. It is considered that these values numerically indicate influence of the histories of the abutments and the box culverts, wherein the abutments have been placed in dry conditions under bridge girders and the box culverts have been placed in wet conditions. In FIG. 11, "R" is a coefficient of correlation and "$R^2$" is a coefficient of determination.

The above abutments and the box culverts investigated are of young material ages and have not been subjected to surface treatments such as water repellant treatments, and therefore, it is considered that the test results meet the Levitt's theoretical equation. However, the concrete surfaces of many actual structures deteriorate due to aging. Therefore, cracks, relatively large apertures or the like are observed on the surface concrete, owing to external factors such as environmental factors, or otherwise, surface treatments such as water repellant treatments are provided on the concrete surfaces. That is, the constants "a" and "n" in the aforementioned formula (2) are values inherent to each of the concrete surfaces, and they are merely idealized values for idealized porous textures. On the other hand, the water absorption properties of the concrete surfaces of the actual structures considerably differ, depending on various factors, such as the environmental conditions (climates, solar radiation, gravity and the like), design conditions, and construction conditions, which are imposed on the actual structures. Therefore, the water absorption properties of the concrete surfaces of the actual structures do not always meet the Levitt's theoretical equation. In addition, even in a case where the water absorption properties meet the Levitt's theoretical equation, it is difficult to obtain or determine the values of the constants "a" and "n" with respect to each of the actual concrete structures on each occasion.

Further, the water absorption properties appearing in the term of time less than 60 seconds (especially, less than 30 seconds) after the beginning of water pouring provide much information, which is considered to include the information in relation with the aforementioned constant "a". The test method of ISAT (the non-patent literature No. 1) and the test method of the non-patent literature No. 2 do not relate to in-situ tests for actual structures. Even if it is assumed that those test methods can be applied to the in-situ tests, the measurements are merely conducted at 10 minutes, 30 minutes and 60 minutes after the beginning of water pouring (the non-patent literature No. 1) or at time intervals in minutes (the non-patent literature No. 2), and therefore, the information as set forth above cannot be obtained therefrom. Further, in the conventional in-situ tests for actual structure (the non-patent literatures Nos. 4 and 5), the term of time between the beginning and the end of the water pouring is long, and even the timing of finishing the water pouring cannot be clarified, and therefore, the water absorption properties of the concrete surface in an initial stage cannot be investigated.

On the other hand, according to the in-situ water absorption test with use of the apparatus 1, the measurement can be started within 15 seconds after the beginning of water pouring, and therefore, the water absorption properties of the concrete surface in the initial stage can be considerably precisely investigated. Thus, the present inventors proposes a water absorption test method of the present invention, wherein the elapsed time and the water absorption rate are measured by the apparatus 1 with the aforementioned arrangement, and wherein identification and comparison of causative factors and evaluative factors in relation with the densification of the surface layer concrete are carried out on the basis of the water absorption rate measured when a predetermined time elapses.

Figure 12:
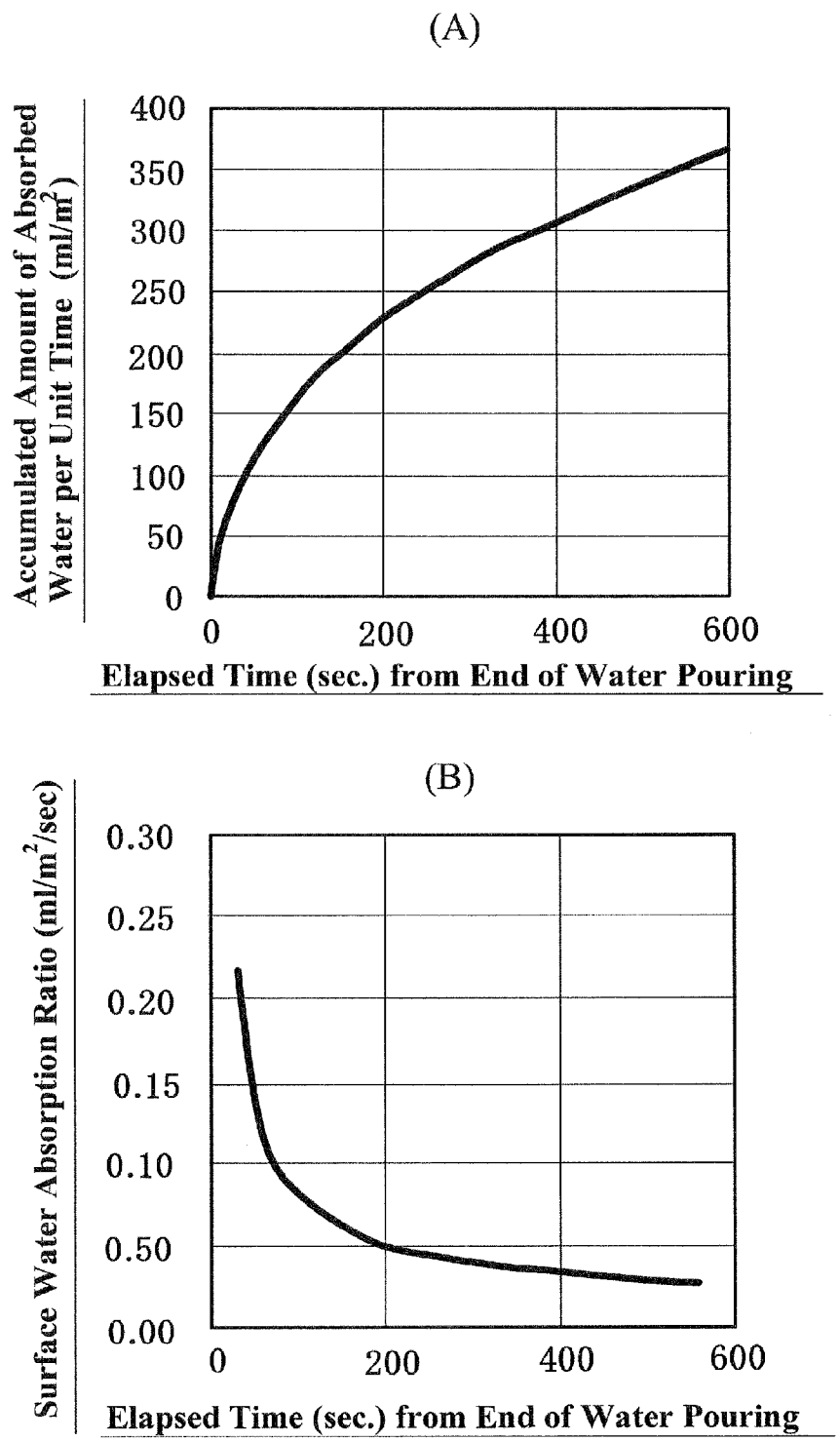

As set forth above, the apparatus 1 can continuously detect and record the variation of the water surface WL in each of the devices 2 by means of the water level measuring means 9. The present inventors carried out the in-situ water absorption tests with respect to a large number of concrete structures with use of the apparatus 1. Typical test results automatically measured in those tests are shown in FIG. 12. FIG. 12(A) shows the time-series variation in the accumulated amount of absorbed water actually measured, and FIG. 12(B) shows the time-series variation in the water absorption rate (the surface water absorption ratio) obtained by differential operation of the variation as shown in FIG. 12(A). It took 5 seconds to finish the water pouring operation actually. However, the starting time of detection (the origin of the x-axis in FIG. 12) was set to be 10 seconds elapsing after the beginning of the water pouring operation.

Figure 13:
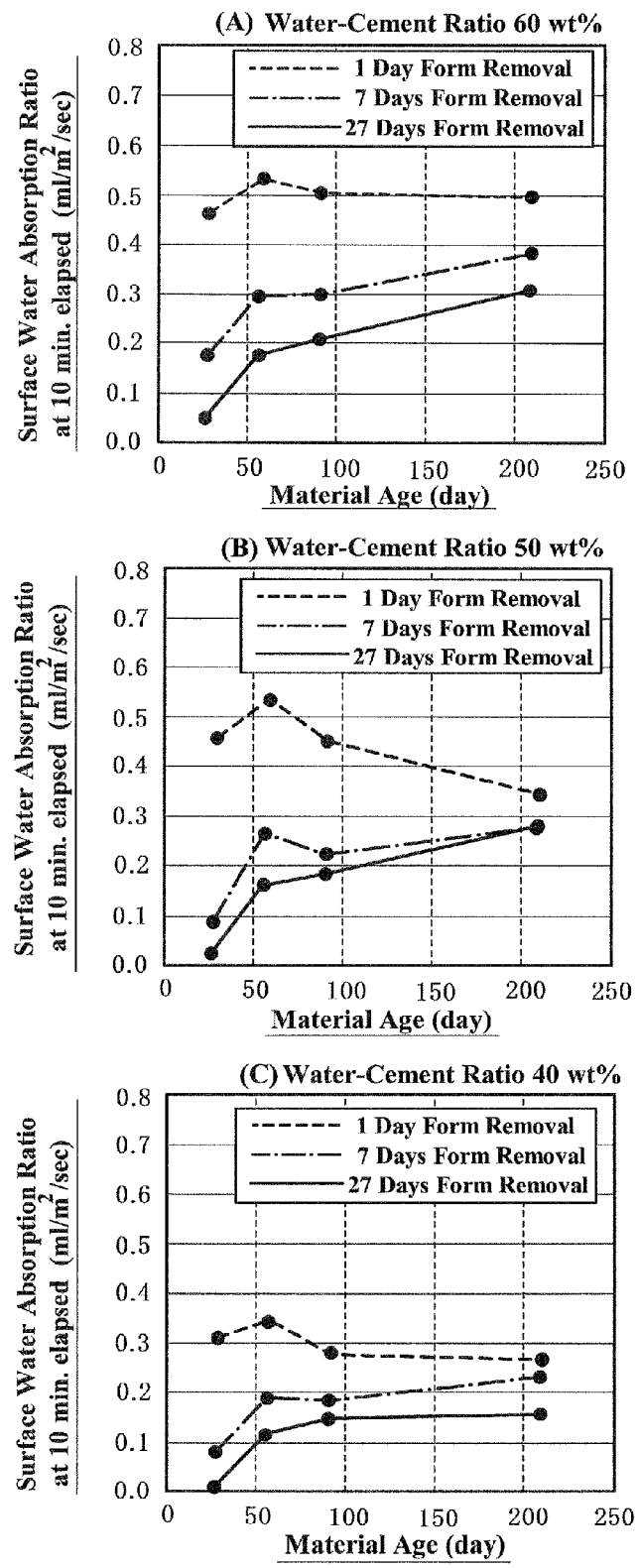
FIG. 13 is a graphic chart showing the relation among the ages of concrete panels, water-cement ratios, terms of time before removal of concrete forms, and the surface water absorption ratios (water absorption rates).
Figure 14:
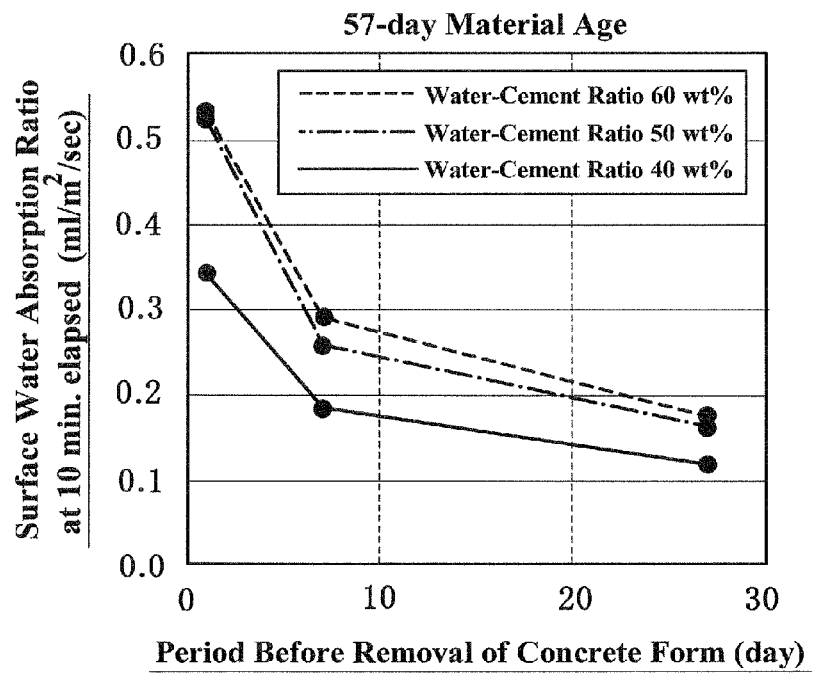
FIG. 14 is a graphic chart showing the relation between days before removal of concrete forms and the surface water absorption ratios (water absorption rates).
Figure 15:
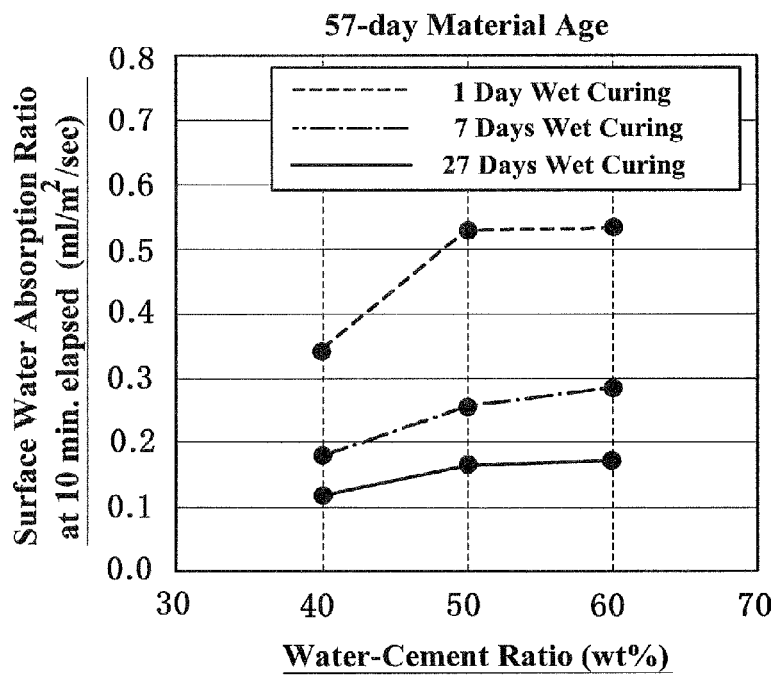
FIG. 15 is a graphic chart showing the relation between the water-cement ratios and the surface water absorption ratios (water absorption rates).

The present inventors performed the in-situ water absorption tests of many concrete panels, which were produced for investigating the effects or functions of the apparatus 1. FIG. 13 includes a graphic charts, each showing the relation among the age of the concrete panel (the days elapsing from concrete placing), the water-cement ratio, the term of time before removal of a concrete form (the curing period), and the water absorption rate (surface water absorption ratio). Each of FIGS. 14 and 15 is a graphic chart showing the test results of the water absorption tests with respect to the concrete panel of 57-day material age. The relation between the days before removal of a concrete form and the water absorption rate (surface water absorption ratio) is shown in FIG. 14. The relation between the water-cement ratio and the water absorption rate (surface water absorption ratio) is shown in FIG. 15. The water absorption rate as shown in FIGS. 13 to 15 is the rate measured at 10 minutes elapsing from the beginning of water pouring. The test results as shown in FIGS. 13 to 15 is those of the concrete panels produced with normal Portland cement. Analogous tendency appears in the test results of the concrete panels produced with Portland blast-furnace cement, class B.

As shown in FIGS. 13 and 14, the water absorption rate differs, depending on the period of time before removal of the concrete form. In each of the different water-cement ratios, the water absorption rate decreases as the period before removal of the concrete form is elongated. This results from the fact that the surface layer concrete has the higher densification as the period before removal of the concrete form is elongated.

Further, as shown in FIGS. 13 and 15, the water absorption rate differs, depending on the water-cement ratio. In each of the different periods before removal of the concrete form, the water absorption rate decreases as the water-cement ratio is reduced. This results from the fact that the surface layer concrete has the higher densification as the water-cement ratio is reduced.

As shown in FIGS. 13 to 15, it is considered that there is a correlation among the water absorption rate at 10 minutes elapsing from the end of water pouring, the water-cement ratio in construction of the concrete and the curing period in construction of concrete (the term of time before removal of the concrete form). Each of the water-cement ratio and the curing period is a kind of causative or evaluative factors closely related to the densification of the surface layer concrete. Therefore, the causative factor or the evaluative factor related to the densification of the surface layer concrete can be obtained from the measurement of the water absorption rate.

Further, in practice, for instance, the aforementioned water absorption tests may be performed with respect to a number of actual structures in which the records of construction works (the water-cement ratios and so forth) still remain. In such a case, a database can be established by statistically processing the elapsed time after the end of water pouring, the water absorption rate, and the causative or evaluative factors such as the water-cement ratios, the curing periods, and so forth. In use of such a database, it is possible to retroactively identify or inspect the conditions of the construction works (water-cement ratios and so forth) by the in-situ water absorption tests with respect to the actual structures in which the records of construction works (water-cement ratios and so forth) have been lost, or buildings which are necessary to retroactively clarify the conditions of construction works.

Furthermore, the densification of the surface layer concrete depends on a mix proportion of the concrete (use of expansive additive or the like), curing method of the concrete, environmental conditions (climates, solar radiation, gravity and the like), a hydration exothermic reaction of cement, a restrained condition of the concrete structure, use of surface-impregnated material (water repellant and the like), and so on. As set forth above, the relation among the water-cement ratio, the curing period and the water absorption rate was analyzed on the basis of the water absorption rate at approximately 10 minutes elapsing from the beginning of water pouring, but it is considered that the other causative or evaluative factors related to the densification of the concrete surface can be clarified by changing or selecting the basis of the water absorption rate for analysis (the reference time and so forth).

The causative or evaluative factors analyzed in accordance with the present invention are exemplified as follows:
[1] Causative Factors
   (1) Mix proportion or proportioning of concrete
   Water-cement ratio
   Water content per unit volume of concrete
   Kind of cement
   Use of admixture
   (2) Properties of fresh concrete (concrete before curing)
   Occurrence or state of bleeding in concrete
   Segregation resistant properties
   (3) Construction work of concrete
   Rate of placing concrete
   Compacting
   Temperature when placing concrete
   Ambient Temperature
   Dimensions and configuration of member
   Restrained condition of members
   Action of environment after removal of concrete form (ambient temperature, action of rain, humidity, influence of solar radiation)
   Curing condition (the term of time before removal of concrete form, positive curing after removal of concrete form (wet curing and so forth))
   (4) Environmental factor
   Ambient temperature, action of rain, humidity, solar radiation
   Material age
[2] Evaluative Factors
   (1) Densification of porous texture of concrete
   (2) Deterioration of densification owing to mesolevel pores
   Cavity under aggregate owing to bleeding phenomenon
   Micro cracks
   Construction joint, placing joint The "kind of cement" means classification of cement, such as normal portland cement, portland blast-furnace cement, low-heat portland cement, high-early strength portland cement, fly ash cement and so forth. Expansive additive, granulated blast-furnace slag fine powder, fly ash and so forth are exemplified as the above admixture. Since the "Dimensions and configuration of member" affect the heat generated by hydration reaction and the bleeding phenomenon, they fall under the causative factors. The "Material age" is the causative factor in relation with progress of hydration reaction, moisture content and so forth. The "Densification of porous texture" is the densification relating to capillary-size pores, since the pores to be evaluated by the surface water absorption test are the capillary-size pores. Damages different from the "Micro cracks", such as visually observable cracks, construction joints and so forth, are matters of water leakage and therefore, such damages are excluded from the above factors.

Figure 16:
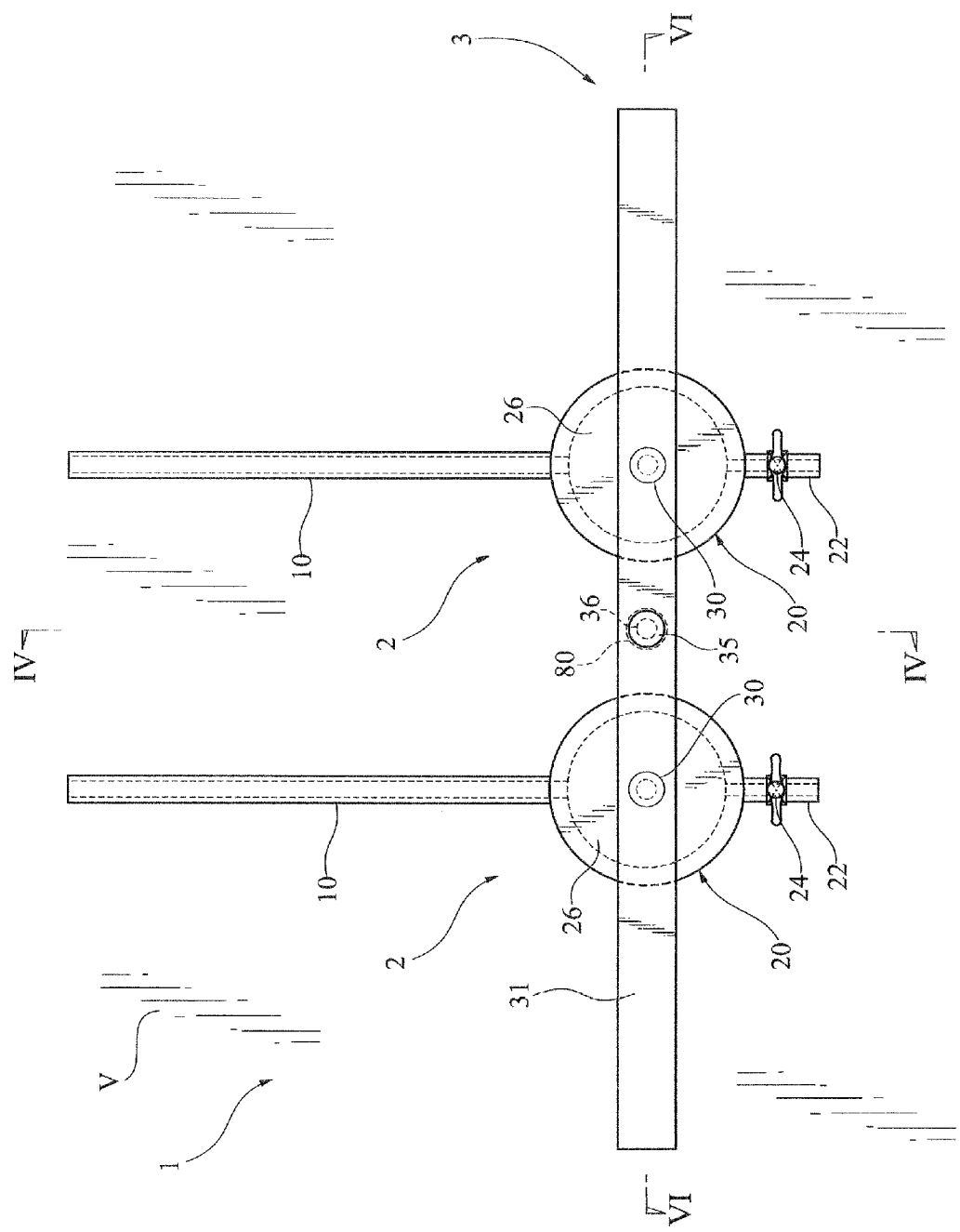
FIG. 16 is a front elevational view showing another mode of use of a position-fixing device as shown in FIGS. 2 to 4.
Figure 17:
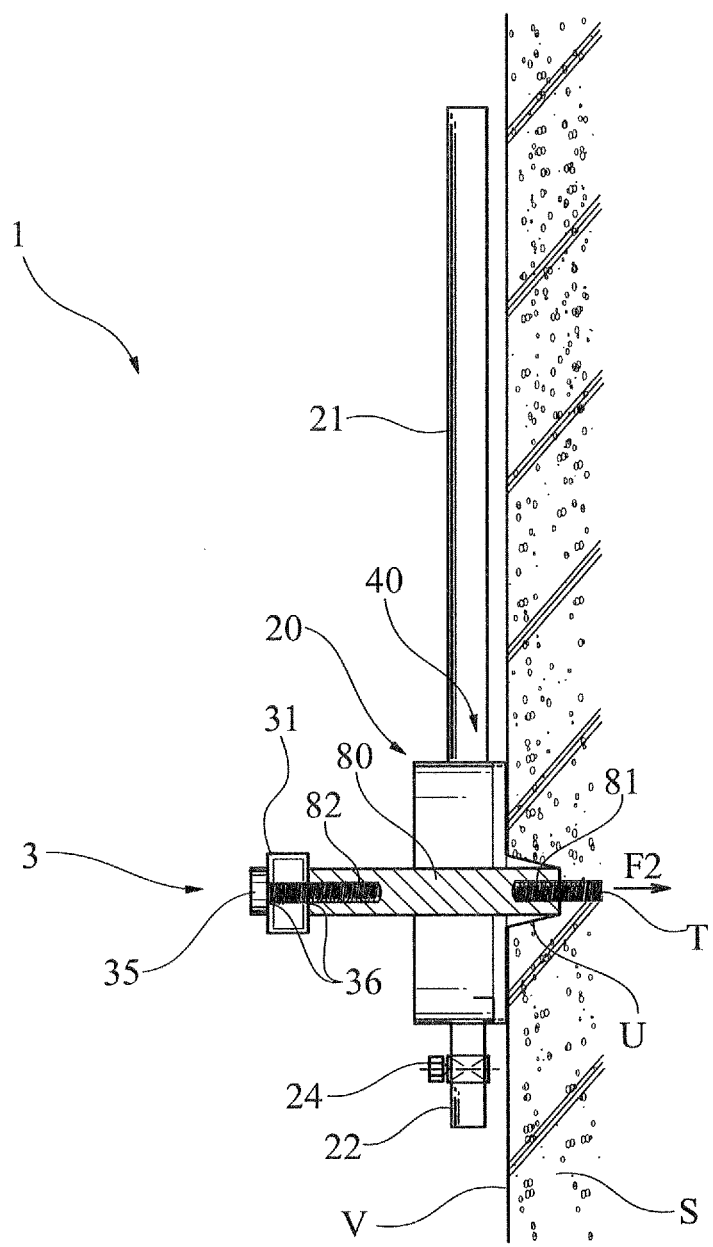
FIG. 17 is a cross-sectional view taken along line IV-IV of FIG. 16.
Figure 18:
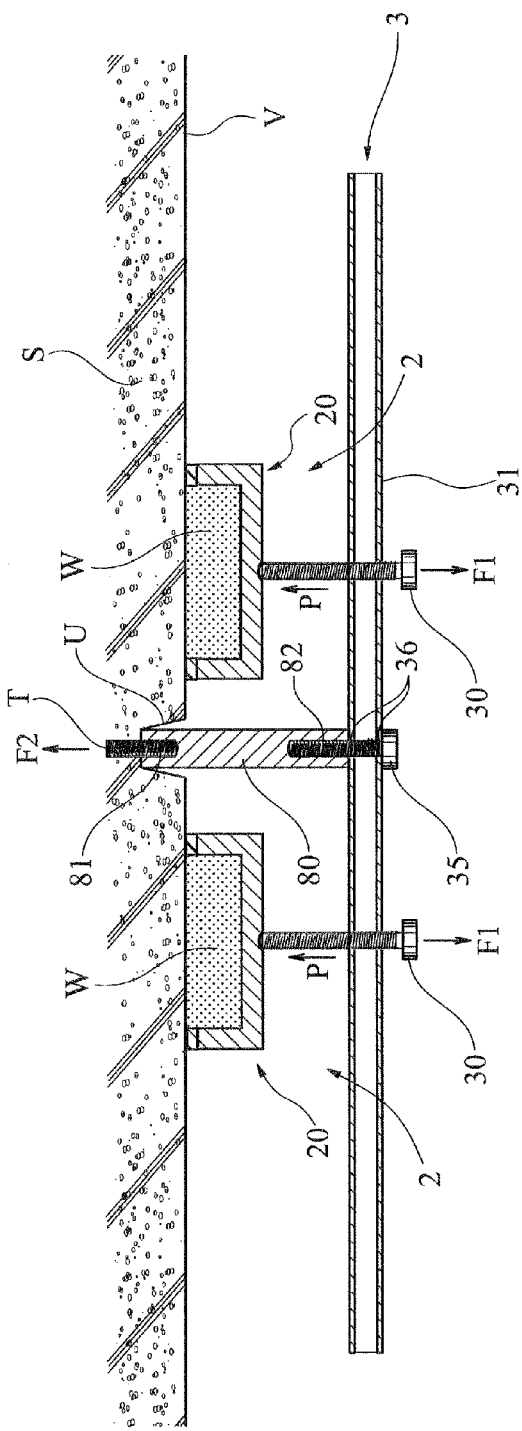
FIG. 18 is a cross-sectional view taken along line VI-VI of FIG. 16.

FIG. 16 is a front elevational view showing another mode of use of the device 3, and FIGS. 17 and 18 are cross-sectional views taken along line IV-IV and line VI-VI of FIG. 16, respectively.

Since the pressure-reducing device 50 is provided with the vacuum pump 51, it is necessary to ensure an electric power source. However, in a condition that the required electric power source is difficult to be prepared near a part of the concrete structure to be tested, the device 50 cannot be used. On the other hand, the concrete structure S is, in general, constructed by pouring a quantity of flowable concrete into a concrete form and removing the form after curing of the concrete, and therefore, separators T used for formwork are embedded in the concrete structure S and they remain therein. An external thread at an end of the separator T appears in a frustoconical bore U after removing a plastic cone.

The device 3 has a through-hole 36 at a center part of the beam 31 as shown in FIGS. 2 and 4(B), in view of the water absorption test conducted in such a step of the construction work (that is, the step before the bore U of the separator T is filled with cement mortar). As shown in FIGS. 17 and 18, an internal thread 81 of a connector bolt 80 is threadedly engaged with an external thread of the separator T. A fixing screw 35 extending through the through-hole 36 is screwed into an internal thread 82 of the bolt 80 and is tightened thereinto. In a case of an existing structure and so forth, the bore U has been already filled with cement mortar, which has already cured. Therefore, in such case, the cement mortar is removed from the bore U and the external thread of the separator T is exposed, and thereafter, the internal thread 81 of the bolt 80 is threadedly engaged with the external thread of the separator T. The removal of the cement mortar from the bore U does not affect the structure of the existing concrete, and therefore, such a water absorption test is considered to fall under or correspond to the completely non-destructive test.

As shown in FIGS. 17 and 18, the screw 35 is tightened so that the beam 31 is securely supported through the bolt 80 by the concrete structure S. The cup 20 presses the annular sealing member 23 against the vertical surface V by tightening the screw 30 of the device 3, so that the sealing member 23 is elastically compressed. As the result, the sealing member 23 is elastically deformed to be brought into intimate contact with the concrete surface (the surface V). Then, the water absorption test is conducted as set forth above. The device 3 and the cup 20 are removed after the test, and the bore U is filled with the cement mortal or the like.

Figure 19:
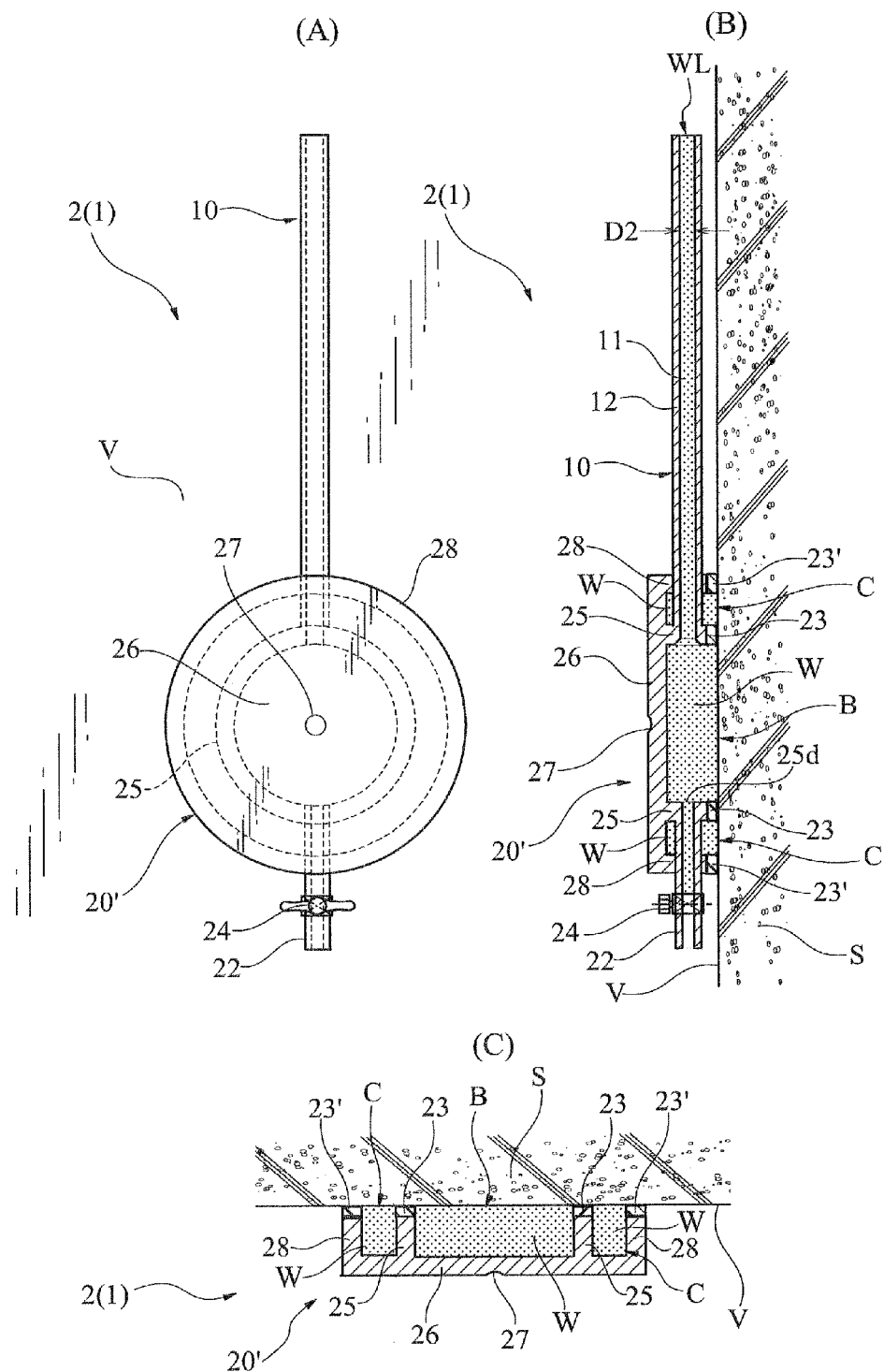
FIG. 19 includes a front elevational view, a vertical cross-sectional view and a horizontal cross-sectional view of the device having a water absorption cup with a double-chamber arrangement.

FIG. 19 includes a front elevational view, a vertical cross-sectional view and a horizontal cross-sectional view showing a modification of the device for water absorption test 2.

The device 2 as shown in FIG. 19 has a water absorption cup 20' with a double chamber arrangement. The cup 20' is additionally provided with an outer peripheral wall 28 outside of the peripheral wall 25. The disc 26 having an enlarged diameter is joined with the wall 28. An annular sealing member 23' is interposed between the wall 28 and the surface V under pressure. Water W (city water) is fed to the inside of the wall 25, so that the water W is filled in the passage 11 up to its top part (the water surface WL).

Figure 20:
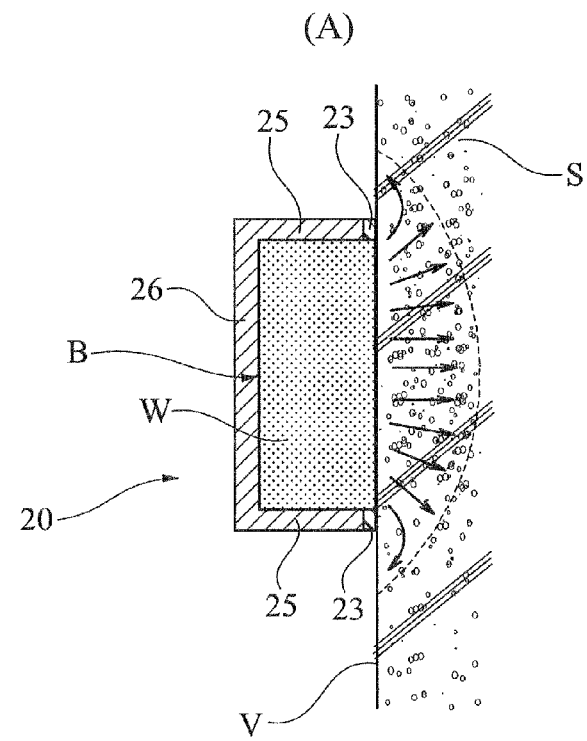
FIG. 20 includes schematic cross-sectional views for explaining a concept of the water absorption cup with the double-chamber arrangement.
Figure 20:
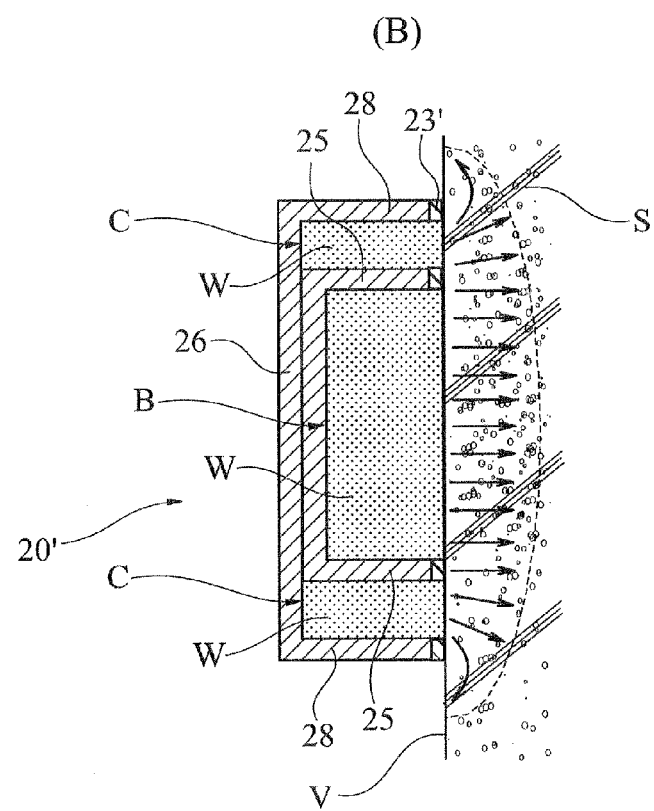

An annular chamber C for absorbed water formed between the walls 25, 28 is filled with water (city water) by a cylinder part (not shown) similar to the cylinder part 10. Comparison between a water absorption mode of the cup 20' and the water absorption mode of the aforementioned cup 20 (FIG. 1) is conceptually illustrated in FIG. 20.

The concrete surface of the actual structure has cracks of approximately 0.01 mm in width, and also, microscopic cracks (micro-cracks) which can be viewed only by a microscope. If the length of the crack on the surface is long, a bypass may be formed by the crack so that the water inside the sealing member 23 is leaked out to the outside thereof. As illustrated in FIG. 20(A), in a case of the cup 20 with a single-chamber arrangement, the water may be leaked out to the outside of the cup 20 and also, its three-dimensional influence may occur. In a case where such an effect of the crack should be excluded, it is preferable that a peripheral area outside the wall 25 (the annular water chamber C) is positively fed with water for restricting the influence of the crack, as shown in FIG. 20(B). The cup 20' as shown in FIG. 19, which has the chamber C located outside the wall 25 and fed with the water W, is based on such a concept. Further, it is considered that a water permeability test can be precisely performed with use of the cup 20' as shown in FIG. 19.

Although the present invention has been described as to preferred embodiments, the present invention is not limited thereto, but may be carried out in any of various modifications or variations without departing from the scope of the invention as defined in the accompanying claims.

For instance, although the position-fixing device is arranged to hold the two devices for water absorption test on the concrete surface in the aforementioned embodiments, the position-fixing device may be arranged to hold the three or more devices for water absorption test.

Further, although the cup is pressed against the concrete surface by the single fixing screw in the aforementioned embodiments, the cup may be pressed thereagainst by the plurality of fixing screws or the other pressing means having an arrangement other than the screw.

Furthermore, in the aforementioned embodiments, the spreading portion of the lower end portion of the cylinder part and so forth are used as the vent means for reduction of the pouring time, or the whole passage of the cylinder part is used as the vent means by pouring the water through the drain tube at the lowermost part of the chamber, but the vent means with the other arrangement, such as an exhaust port additionally provided on the cup, may be used for reduction of the water pouring time.

INDUSTRIAL APPLICABILITY

The present invention can be preferably applied to the in-situ water absorption test for measuring the water absorption property of the concrete surface of the actual structure. Especially, the present invention can be preferably applied to a water absorption test for carrying out identification or comparison of the causative or evaluative factors (construction conditions, design conditions, environmental conditions of concrete structures, and so forth) which relate to the densification of the surface layer concrete. According to the present invention, the densification of the surface layer concrete can be evaluated by means of the in-situ water absorption test, and also, it is possible to obtain the information on quality of design or construction work, environment surrounding the concrete structure, and so forth. Thus, usefulness of the present invention is remarkable.

LIST OF REFERENCE NUMERALS 1 apparatus for water absorption test
2 device for water absorption test
3 position-fixing device
6 water supply appliance
7 flexible tubes for water pouring
9 water level measuring means
10 cylinder part
20, 20' water absorption cup
30 fixing screw
40 sucker
50 pressure-reducing device
60 cylindrical container
70 fitting or connector
80 connector bolt
90 water pressure sensor
90a detecting element
91 automatic recording system
92 control signal line
B absorbed water chamber
E suction chamber
L vertical distance
S concrete structure
V vertical surface
LL horizontal surface
W water
HL initial water level
WL water surface

The invention claimed is:

1. A method for a water absorption test of a concrete surface, in which an edge portion of an opening part of a water absorption cup is brought into intimate contact with the concrete surface of a concrete structure, water for the test is poured into a water absorption chamber in the cup, and an amount of water absorbed from the chamber by the concrete structure is measured in situ;
   said test being a non-destructive test,
   wherein the amount of water held in said chamber is continuously detected or successively detected at small time intervals, in order to measure a water absorption rate and elapsed time from an end of water-pouring into the chamber,
   wherein identification or comparison of causative or evaluative factors related to densification of a surface layer portion of concrete is carried out on the basis of the water absorption rate measured at a predetermined elapsed time, and
   wherein a water pouring operation is finished within 15 seconds and measurement of the amount of water absorbed by said concrete surface is started within 15 seconds after beginning of the water-pouring into the chamber.

2. A method according to claim 1, wherein said factor is a water-cement ratio of concrete in a concrete placement work, or a term of time between finish of the concrete placement work and removal of a concrete form.

3. A method according to claim 1, wherein said time interval is equal to or less than 10 seconds.

4. A method according to claim 1, wherein said opening part has an area equal to or larger than 5000 mm$^2$.

5. A method according to claim 1, wherein said cup is integrally connected to said concrete surface by means of a negative pressure acting on the concrete surface or a mechanical connection with an existing threaded member embedded in said concrete structure.

6. A method according to claim 1, wherein the water in said cup is pressurized up to a predetermined pressure so that an amount of water permeating into said concrete surface is measured.

7. A method for a water absorption test of a concrete surface, in which an edge portion of an opening part of a water absorption cup is brought into intimate contact with the concrete surface of a concrete structure, water for the test is poured into a water absorption chamber in the cup, and an amount of water absorbed from the chamber by the concrete structure is measured in situ;
   wherein the amount of water held in said chamber is continuously detected or successively detected at small time intervals, in order to measure a water absorption rate and elapsed time from an end of water-pouring into the chamber,
   wherein identification or comparison of causative or evaluative factors related to densification of a surface layer portion of concrete is carried out on the basis of the water absorption rate measured at a predetermined elapsed time,
   wherein a water pouring operation is finished within 15 seconds and measurement of the amount of water absorbed by said concrete surface is started within 15 seconds after beginning of the water-pouring into the chamber; and
   wherein said amount of absorbed water is detected by a water pressure in said chamber.

8. An apparatus for a water absorption test of a concrete surface, which is intended for a non-destructive water absorption test of a concrete structure and which has a water absorption cup provided with a water absorption chamber to be filled with water for an in-situ water absorption test by pouring water into the chamber, wherein said cup has an opening part surrounded by an edge which can be in intimate contact with the concrete surface, and the water in said chamber is in contact with said concrete surface through the opening part and is absorbed by the concrete surface, comprising:
   a detecting device provided with a detecting element for continuously detecting an amount of water held in said chamber, or successively detecting said amount of water at small time intervals,
   a measuring device which indicates or records an amount of absorbed water and elapsed time from an end of water-pouring into the chamber, wherein a result detected by said detecting device is input into the measuring device, and
   a position-fixing device for fixing a position of said cup, which is provided with a transverse beam spaced apart from said concrete surface, a pressing device carried by the beam and pressing said cup against the concrete surface, and a holding device for keeping a position of the beam and integrally connecting the beam to said concrete structure,
   wherein said detecting device is a water pressure sensor which detects a water pressure in said chamber.

9. An apparatus according to claim 8, wherein a detecting element of said sensor is inserted into said chamber to detect the water pressure at or near a lowermost part of said chamber.

10. An apparatus according to claim 8, wherein said measuring device has converting means for converting a value detected by said sensor to said amount of absorbed water, and means for calculating a water absorption rate on the basis of change or variation in the amount of absorbed water per unit time.

11. An apparatus for a water absorption test of a concrete surface, which is intended for a non-destructive water absorption test of concrete structure and which has a water absorption cup provided with a water absorption chamber to be filled with water for an in-situ water absorption test by pouring the water into the chamber, wherein said cup has an opening part surrounded by an edge which can be in intimate contact with the concrete surface, and the water in said chamber is in contact with said concrete surface through the opening part and is absorbed by the concrete surface, comprising:
   a detecting device which is provided with a detecting element for continuously detecting an amount of water held in said chamber, or successively detecting said amount of water at small time intervals, and which starts detection of said amount of water before one minute elapses from beginning of water-pouring into the chamber,
   a measuring device which indicates or records an amount of absorbed water and elapsed time from an end of water-pouring into the chamber, wherein a result detected by said detecting device is input into the measuring device, and
   a position-fixing device for fixing a position of said cup, which is provided with a transverse beam spaced apart from said concrete surface, a pressing device carried by the beam and pressing said cup against the concrete surface, and a holding device for keeping a position of the beam and integrally connecting the beam to said concrete structure.

12. An apparatus according to claim 11, wherein said holding device is provided with a sticking means which sticks to the surface of said concrete structure under a negative pressure, or mechanical connector means which is threadedly engaged with an existing threaded member embedded in the concrete structure, and wherein the sticking means or the connector means connects said beam with the concrete structure by a force, which exceeds a reaction force of said pressing device acting on the beam.

13. An apparatus according to claim 12, wherein said sticking means includes a sticking part which can stick on said concrete surface, a negative pressure chamber sealingly confined between the sticking part and the concrete surface, and connecting means for connecting the negative pressure chamber to a pressure-reducing device which sucks air in the negative pressure chamber.

14. An apparatus according to claim 12, wherein said existing threaded member is a separator at least partially embedded in said concrete structure, and said connector means is a connector provided with a threaded portion threadedly engaged with a thread of the separator.

15. An apparatus according to claim 11, wherein said opening part has an area equal to or larger than 5000 mm$^2$.

16. An apparatus according to claim 11, wherein said cup has vent means for urging exhaust of air bubbles in said water absorption chamber when pouring the water thereinto.

17. An apparatus according to claim 11 wherein said cup is further provided with pressurizing means so that the water in the cup is pressurized up to a predetermined pressure for measuring an amount of water permeating into said concrete surface.

* * * * *